(12) United States Patent
Darrah et al.

(10) Patent No.: US 12,399,139 B1
(45) Date of Patent: Aug. 26, 2025

(54) SYSTEMS AND METHODS FOR EVALUATING HYDROGEN GENERATION POTENTIAL FROM ROCKS FOR NATURAL HYDROGEN EXPLORATION

(71) Applicant: Koloma, Inc., Denver, CO (US)

(72) Inventors: Thomas Darrah, Westerville, OH (US); Brent Lary, Columbus, OH (US); Christopher Gardner, Columbus, OH (US); Colin Whyte, Grove City, OH (US); William Eymold, Columbus, OH (US)

(73) Assignee: Koloma, Inc., Denver, CO (US)

( * ) Notice: Subject to any disclaimer, the term of this patent is extended or adjusted under 35 U.S.C. 154(b) by 0 days.

(21) Appl. No.: 18/943,580

(22) Filed: Nov. 11, 2024

Related U.S. Application Data

(60) Provisional application No. 63/713,042, filed on Oct. 28, 2024.

(51) Int. Cl.
*G01N 23/095* (2018.01)
*G01N 33/24* (2006.01)

(52) U.S. Cl.
CPC .......... *G01N 23/095* (2018.02); *G01N 33/24* (2013.01)

(58) Field of Classification Search
CPC .............................. G01N 23/095; G01N 33/24
See application file for complete search history.

(56) References Cited

FOREIGN PATENT DOCUMENTS

WO  WO-2008128331 A1 * 10/2008 ............. C09K 8/582

* cited by examiner

*Primary Examiner* — Jurie Yun
(74) *Attorney, Agent, or Firm* — K&L Gates LLP

(57) ABSTRACT

The mineralogical, chemical, magnetic, and physical properties of a rock can be used to determine the amount of hydrogen that was generated during rock alteration and the remaining amount of hydrogen generation potential. The methodologies evaluate the hydrogen generation potential of geological samples and identify natural hydrogen source rocks. The mineralogy, elemental composition, iron content and oxidation state, and other properties of a geological sample may be determined. From the determined mineralogy and other properties of the geological sample, the amount of hydrogen which the geological sample may have generated may be quantified. This method can determine the maturity of hydrogen source rocks, the potential volume of hydrogen that can be generated in other parts of a given geologic province with higher degrees of hydrogen source rock maturity, and quantify the potential remaining volume of hydrogen that can be still be generated via secondary enhanced hydrogen stimulation processes.

11 Claims, 13 Drawing Sheets

Serpentinization Reactions

| Mineral | Mineral Phase | Serpentinization Reaction | Moles of Igneous Minerals | Moles of $H_2$ Generated | Moles of Magnetite Produced |
|---|---|---|---|---|---|
| Olivine | Fayalite | $3Fe_2SiO_4 + 2H_2O \rightarrow 2Fe_3O_4 + 3SiO_2 + 2H_2$ | 3 | 2 | 2 |
| Pyroxene | Ferrosilite | $3Fe_2Si_2O_6 + 2H_2O \rightarrow 2Fe_3O_4 + 6SiO_2 + 2H_2$ | 3 | 2 | 2 |

Carbonation Reactions

| Mineral | Mineral Phase | Reaction | Moles of Igneous Materials | Moles of $CO_2$ Sequestered |
|---|---|---|---|---|
| Olivine | Forsterite | $Mg_2SiO_4 + 2CO_2 \rightarrow 2MgCO_3 + SiO_2$ | 1 | 2 |
| Pyroxene | Enstatite | $Mg_2Si_2O_6 + 2CO_2 \rightarrow 2MgCO_3 + 2SiO_2$ | 1 | 2 |
| Plagioclase | Anorthite | $CaAl_2Si_2O_8 + CO_2 + 2H_2O \rightarrow CaCO_3 + Al_2Si_2O_5(OH)_4$ | 1 | 1 |
| Serpentine | Antigorite | $Mg_3Si_2O_5(OH)_4 + 3CO_2 \rightarrow 3MgCO_3 + 2SiO_2 + 2H_2O$ | 1 | 3 |
| Brucite | | $Mg(OH)_2 + CO_2 \rightarrow MgCO_3 + 2H_2O$ | 1 | 1 |

Sulfidation Reactions

| Reaction | Moles of Iron (II) Reacted | Moles of $H_2$ Generated | Moles of $H_2S$ Sequestered |
|---|---|---|---|
| $FeS + H_2S \rightarrow FeS_2 + H_2$ | 1 | 1 | 1 |
| $Fe_{2+} + 2H_2S \rightarrow FeS_2 + H_2 + 2H^+$ | 1 | 1 | 2 |
| $Cu^+ + Fe^{2+} + 2H_2S \rightarrow CuFeS_2 + 0.5H_2 + 3H^+$ | 1 | 0.5 | 2 |

Fig. 1

| Mineral Classification Scheme | Description | Examples |
|---|---|---|
| $H_0$ | Primary minerals not directly involved in hydrogen generation | Quartz, Plagioclase, Calcite, Gypsum |
| $H_1$ | Primary (unaltered) minerals that potentially generate hydrogen | Olivine, Pyroxene |
| $H_2$ | Secondary (altered) minerals that generated hydrogen previously | Chlorite, Hematite, Magnetite |
| $H_{2a}$ $H_{2b}$ | Secondary (altered) minerals that can react to generate hydrogen again Secondary (altered) minerals that cannot generate hydrogen again | Magnetite Hematite, Lizardite |

Fig. 3

| Primary Mineral Assemblage (H₁) | Fe/Mg | Fe-rich Endmember |
|---|---|---|
| Augite | * | Pigeonite |
| Clinopyroxene | * | Hedenbergite |
| Orthopyroxene | * | Ferrosilite |
| Fe-Amphiboles | * | |
| Fe-Spinels | * | |
| Olivine | * | Fayalite |
| Ilmenite | | |

| Secondary Mineral Assemblage (H₂) | Fe/Mg | Fe²⁺/Fe³⁺ |
|---|---|---|
| Antigorite | * | * |
| Celadonite | | |
| Chrysotile | * | * |
| Clinochlore | * | * |
| Cordierite | * | * |
| Crostedtite | | |
| Epidote | * | * |
| Fe-Garnets | * | |
| Fe-Spinels | * | |
| Glauconite | | |
| Geothite | | |
| Hematite | | |
| Kaolinite | * | * |
| Lizardite | * | * |
| Maghemite | | |
| Magnetite | | |
| Prehnite | * | * |
| Pumpellyite | * | * |
| Siderite | | |
| Smectite/Nontronite | * | * |
| Vermiculite | | |

Fig. 6

| Scenario | [FeO]+[Fe₂O₃] | [MgO] | [SiO₂] | Reacts with HCl | Interpretation | Source Rock |
|---|---|---|---|---|---|---|
| 1 | >4% | >4% | <60% | Yes | Quality source rock, alteration occurred | Conventional |
| 2 | >4% | >4% | <60% | No | Quality source rock, no alteration occurred | EHP |
| 3 | <4% | <4% | >60% | N/A | Poor source rock, irrelevant alteration | No |

Fig. 11

SYSTEMS AND METHODS FOR EVALUATING HYDROGEN GENERATION POTENTIAL FROM ROCKS FOR NATURAL HYDROGEN EXPLORATION

CROSS-REFERENCE TO RELATED APPLICATIONS

This application claims benefit to U.S. Provisional Application No. 63/713,042, filed Oct. 28, 2024, the entire disclosure of which is incorporated by reference herein.

FIELD OF THE INVENTION

Embodiments of the present disclosure relate generally to the field of energy extraction, geology, geochemistry, mineralogy, geologic hydrogen extraction, subsurface geologic hydrogen stimulation, or subsurface carbon sequestration by carbon mineralization or sulfur sequestration by sulfur mineralization. Some embodiments disclose methods of evaluating rock material for elemental, chemical (e.g., oxide), or mineralogical composition in order to evaluate the volume of hydrogen that was or can be derived from a given rock sample for the purposes outlined above and below. More particularly, the present disclosure relates to methods for identifying, evaluating, and high-grading rocks associated with past generation of hydrogen from geologic materials to improve exploration for geologic hydrogen, to identify target lithologic intervals for subsurface hydrogen stimulation, referred to herein as enhanced hydrogen production (EHP), to identify lithologic intervals for carbon or sulfur mineralization, or combinations thereof.

This section is intended to introduce various aspects of the technical field, which may be associated with embodiments described in this disclosure. Thus, the forgoing discussion in this section provides a framework for better understanding the disclosure, and is not to be viewed as an admission of prior art.

BACKGROUND

The following section is intended to introduce terminology and context associated with embodiments described in this disclosure. Thus, the following discussion in this section provides a framework for better understanding the disclosure, and is not to be viewed as an admission of prior art.

Hydrogen is a carbon-free energy carrier and chemical feedstock that has the potential to supplant fossil fuels, especially when combined with other sources. Hydrogen can be generated using sustainable energy sources such as geothermal, solar, wind, and hydroelectric power. The disclosure herein relates to hydrogen produced from or generated (naturally or through the introduction of various fluids) within the subsurface by drilling, boring, mining, or various other means of penetrating the earth.

In the production of natural resources from formations within the earth, a well or borehole is drilled into the earth to the location where the natural resource is believed to be located. These natural resources may be hydrogen, helium, carbon dioxide, nitrogen, dihydrogen sulfide, methane, or other hydrocarbon gases; a dihydrogen sulfide reservoir, a hydrogen reservoir, a helium reservoir, a carbon dioxide reservoir, a natural gas reservoir, a reservoir rich in dihydrogen sulfide, a reservoir rich in hydrocarbons, a reservoir rich in helium; the natural resource may be fresh water, brackish water, or brine; it may be a heat source for geothermal energy; or it may be some other natural resource, ore deposit, mineral, metal, or gem that is located within the ground.

These resource-containing formations may be a few hundred feet, a few thousand feet, or tens of thousands of feet below the surface of the earth, including under the floor of a body of water (e.g., below the sea floor) or beneath other natural resources (e.g., below aquifers, lakes, mines). In addition to being at various depths within the earth, these formations may cover areas of differing sizes, shapes, and volumes.

Typically, and by way of general illustration, in drilling a well an initial borehole is made into the earth (e.g., the surface of land or seabed), and then subsequent and smaller diameter boreholes are drilled to extend the overall depth of the borehole. In this manner as the overall borehole gets deeper its diameter becomes smaller, resulting in what can be envisioned as a telescoping assembly of holes with the largest diameter hole being at the top of the borehole closest to the surface of the earth.

Thus, by way of example, the starting phases of a subsea drill process may be explained in general as follows. Once the drilling rig is positioned on the surface of the water over the area where drilling is to take place, an initial borehole is made by drilling a 36" hole in the earth to a depth of about 200-300 ft. below the seafloor. A 30" casing is inserted into this initial borehole. This 30" casing may also be called a conductor. The 30" conductor may or may not be cemented into place. During this drilling operation a riser is generally not used and the cuttings from the borehole (e.g., the earth and other material removed from the borehole by the drilling activity) are returned to the seafloor. Next, a 26" diameter borehole is drilled within the 30" casing, extending the depth of the borehole to about 1,000-1,500 ft. This drilling operation may also be conducted without using a riser. A 20" casing is then inserted into the 30" conductor and 26" borehole. This 20" casing is cemented into place. The 20" casing has a wellhead secured to it. (In other operations an additional smaller diameter borehole may be drilled, and a smaller diameter casing inserted into that borehole with the wellhead being secured to that smaller diameter casing.) A blow out preventer (BOP) is then secured to a riser and lowered by the riser to the sea floor, where the BOP is secured to the wellhead. From this point forward, all drilling activity in the borehole takes place through the riser and the BOP.

It should be noted that subsea drilling operations that do not employ a riser are also contemplated.

For a land-based drill process, the steps are similar, although the large diameter tubulars, 30"-20" are typically not used. Thus, and generally, there is a surface casing that is typically about 13⅜" diameter. This may extend from the surface, (e.g., wellhead and BOP) to depths of tens of feet to hundreds of feet. One of the purposes of the surface casing is to meet environmental requirements to protect ground water by preventing surface casing ventflow to groundwater aquifers or prevent surface casing ventflow of greenhouse gases or flammable gases to groundwater aquifers or the atmosphere. The surface casing should have sufficiently large diameter to allow the drill string, production equipment (e.g., electronic submersible pumps (ESPs)), and circulation mud to pass through. Below the casing, one or more different diameter intermediate casings may be used. (It is understood that sections of a borehole may not be cased and are referred to as open hole.) These can have diameters in the range of about 9" to about 7", although larger and smaller sizes may be used, and can extend to depths of thousands and tens of thousands of feet.

The section of the well located within the reservoir (i.e., the section of the formation containing the natural resources) can be called the pay zone. The production tubing is placed inside the casing and extends from a pay zone, or production zone of the borehole up to and through the wellhead on the surface. There may be a single production tubing or multiple production tubings in a single borehole, with each of the production tubing endings being at different depths.

Fluid communication between the formation and the well or borehole can be greatly increased by the use of perforations, hydraulic fracturing, or other stimulation techniques. The first uses of hydraulic fracturing date back to the late 1940s and early 1950s. In general, hydraulic fracturing treatments involve forcing fluids down the well or borehole and into the formation, where the fluids enter the formation and crack, e.g., by forcing the layers of rock to break apart or fracture. These fractures create channels or flow paths that may have cross sections of a few microns, to a few millimeters, to several millimeters in size, and potentially larger. The fractures may also extend out from the well in all directions for a few feet, several feet, and tens of feet or further. The fractures may be kept open by using a proppant (e.g., various sized sand or other mineral grains) that are forced down the well with the fracturing fluid in a single operation. It should be remembered that the longitudinal axis of the well or borehole in the reservoir may not be vertical: it may be on an angle (either sloping up or down) or it may be horizontal.

During the drilling of wells or boreholes, drilling fluids (i.e., water-based mud, oil-based mud, water, foam, aerated mud, air, synthetic fluids, or other fluids), herein referred to as "drilling fluid," are often pumped down the borehole through the drill string and out into the borehole at the drill bit, then back up to the surface between the exterior of the drill string and the borehole wall. In some drilling operations, air or aerated fluid is injected through the drill string in a similar manner and can return formation fluids, including gases, to the surface. In the case where drilling fluid is used, it can lubricate the borehole, drill bit, and drill string, and prevent thermal degradation of the drill bit, as well as provide a medium through which to eject drilled rock (e.g., cuttings), sediment material, or formation fluids (e.g., gases) up the borehole to the surface.

In some examples, the subsurface rock formation from which gases are extracted can include at least one of sedimentary rocks (e.g., sandstone, limestone, shales, graywacke, evaporites), metamorphic rocks (e.g., serpentinites, marbles), igneous rocks (e.g., dunite, pyroxenite, basalt, gabbro, granite, or others), or from formations containing overly thermally mature hydrocarbon fluids, hydrocarbon source rocks, coal, or graphite. Other examples can include iron-rich rock, mafic or ultramafic igneous rock, metamorphosed or hydrothermally altered mafic or ultramafic igneous rock, olivine- or pyroxene-bearing igneous, metamorphic, or sedimentary rock or sediment, metamorphosed or hydrothermally altered olivine- or pyroxene-bearing igneous, metamorphic, or sedimentary rock or sediment, serpentine mineral-bearing rock or sediment, partially or completely serpentinized rock, serpentinite, amphibole-rich igneous or metamorphic rock, amphibolite, pyrite-bearing rock, iron-rich or other metalliferous ore deposit, iron-rich sandstone, other iron-rich sedimentary rock, or iron-rich sediments.

In some examples, the source of hydrogen can include any of the sources described above (e.g., mafic or ultramafic rock) that is drilled, drilled and stimulated (e.g., hydraulic fracturing or perforation), drilled and stimulated (e.g., hydraulic fracturing or perforation) with the accompanying introduction of heat, chemicals, or fluids (e.g., water, carbon dioxide, dihydrogen sulfide), or fluids encountered while interacting with various subsurface reservoirs or geothermal systems, mining operations, water well drilling, formation waters, or any fluids exsolved from processes related to their exploration, characterization, or extraction.

BRIEF SUMMARY

Embodiments of the present disclosure relate generally to the field of energy extraction, geology, geochemistry, mineralogy, geologic hydrogen extraction, subsurface geologic hydrogen stimulation, or subsurface carbon sequestration by carbon mineralization or sulfur sequestration by sulfur mineralization.

The present disclosure relates to methods for obtaining a sample of a geological source rock, determining a concentration and a species of iron in the geological sample, and quantifying a volume of past hydrogen generation based on the concentration and the species of iron. These measurements can be obtained through field and laboratory analyses of drilled material (e.g., cuttings, whole core, rotary sidewall core) or rocks or sediments collected at the surface. The results of these analyses will be used to evaluate the source rock potential and source rock maturity of these materials regarding the generation of hydrogen for the purposes of exploration for geologic hydrogen and the construction of geologic hydrogen exploration models.

The present disclosure further relates to methods for obtaining a sample of a geological source rock, determining a mineralogy of the geological sample, and quantifying a volume of hydrogen generation based on the mineralogy. These measurements can be obtained through field and laboratory analyses of drilled material (e.g., cuttings, whole core, rotary sidewall core) or rocks or sediments collected at the surface. The results of these analyses will be used to evaluate the source rock potential and source rock maturity of these materials regarding the generation of hydrogen for the purposes of exploration for geologic hydrogen and the construction of geologic hydrogen exploration models.

The systems and methods disclosed herein relate to methods and systems for improving the construction of geologic hydrogen exploration models and understanding of the geologic hydrogen system.

The systems and methods disclosed herein relate to methods for identifying, evaluating, and high-grading source rocks associated with the generation of geologic hydrogen using high-resolution measurements of mineralogy, chemical oxide, and other rock or mineralogical qualities (e.g., color, density, magnetic susceptibility, oxidation state) to calibrate, integrate, and improve the development of geophysical or geochemical models and subsurface interpretations.

The systems and methods disclosed herein relate to methods and systems that use mineralogic measurements (e.g., normative or modal mineralogy) to estimate past or predict future hydrogen generation on a molar or volumetric basis.

The systems and methods disclosed herein relate to determining oxide data, carbonate reactivity, or sulfur reactivity of the geological sample, wherein the oxide data includes one or more of iron, magnesium, and silica data, and utilizing the geological source rock for natural hydrogen exploration based on the oxide data, carbonate reactivity, or sulfur reactivity. Through a combination of the oxide data, carbonate reactivity, or sulfur reactivity of the geological sample, a Hydrogen Alteration Index is further established herein.

The systems and methods disclosed herein relate to methods and systems for improving the characterization of a rock based on its suitability as a hydrogen source rock by detecting evidence of alteration for past hydrogen generation and accumulation and/or identifying targets for conventional hydrogen exploration or a combination of both.

Embodiments include devices and methods for identifying hydrogen source rocks, geologic settings, key stratigraphic intervals or zones, or intervals where hydrogen has been generated, where hydrogen has been generated and accumulated, or where hydrogen can be generated. Other related embodiments include devices and methods for improving data processing and interpretation methods for evaluation of hydrogen source rock potential and maturity based on the use of chemical, mineralogical, or other rock properties (e.g., density, magnetic character) measurements conducted on rocks or materials collected at the surface, through subsurface drilling (e.g., cuttings, core), or measured through downhole logging for the purposes of exploration for geologic hydrogen.

The systems and methods disclosed herein relate to determining a density of a geological sample, determining a coloration of a sample, and determining the geological sample's quality as a hydrogen source rock based on the density and the coloration. Both of these parameters-density and coloration—of geological samples can provide information regarding the potential usefulness of a geological sample as a hydrogen source rock. By considering both of these data points in combination, the Color-Density Index is established herein.

In some embodiments, the techniques described herein relate to a method for evaluating hydrogen generation potential from a geological source rock. The method includes: obtaining a geological sample of the geological source rock; determining one or more properties of iron in the geological sample; and performing a hydrogen quantification operation based on the one or more properties of iron to determine a potential for hydrogen production without injection of a reactant. The one or more properties of iron in the geological sample are determined by measuring, via Mössbauer spectroscopy, an abundance of $Fe^{3+}$ and an abundance of $Fe^{2+}$ in the geological sample.

In some aspects, the one or more properties of iron in the geological sample is a concentration of iron. In other aspects, the one or more properties of iron in the geological sample is a species of iron. In some embodiments, the species of iron includes one of a mineral or an oxidation state.

In some aspects, the step of determining the one or more properties of iron includes measuring minerals of the geological sample through one of: i. using x-ray diffraction, scanning electron microscope-energy dispersive X-ray spectroscopy, or optical mineralogy, ii. measuring an abundance of minerals with $Fe^{2+}$, directly measuring an iron content using x-ray fluorescence, neutron activation, Inductively Coupled Plasma Mass Spectrometry (ICP-MS), and Inductively Coupled Plasma Optical Emission Spectrometry (ICP-OES) of the geological sample, and apportioning the iron content between the minerals with $Fe^{2+}$; iii. measuring an abundance of minerals with $Fe^{2+}$, separating the minerals with $Fe^{2+}$, and directly measuring an iron content of individual phases of minerals without $Fe^{2+}$; or iv. measuring an iron content using x-ray fluorescence, neutron activation, ICP-MS, or ICP-OES, for example, as combined directly with the use of Mössbauer spectroscopy to measure $Fe^{3+}$ and $Fe^{2+}$ in the geological sample.

In some embodiments, the step of performing the hydrogen quantification operation includes quantifying a volume of hydrogen generated over geologic time or quantifying a potential volume of hydrogen that may be generated. In some embodiments, the step of quantifying the potential volume of hydrogen that may be generated includes calculating the hydrogen generation according to an equation $M_1$ calculated for each mineral: where $m_{rock}$ is the mass of sample being analyzed, $\mu_i$ is the relative abundance of mineral i in the sample, $MW_i$ is the molecular weight of mineral i in kg/mol, and oi is the stoichiometric ratio of moles of hydrogen generated from moles of mineral i, and wherein the equation $M_1$ is calculated for each mineral of the geological sample.

In some embodiments, the hydrogen generated over geologic time or the potential volume of hydrogen that may be generated exhibits a carbon intensity score less than 3.0 kg $CO_{2eq}$/kg $H_2$. In some embodiments, the hydrogen generated over geologic time or the potential volume of hydrogen that may be generated exhibits a carbon intensity score less than 1.5 kg $CO_{2eq}$/kg $H_2$. In some embodiments, the hydrogen generated over geologic time or the potential volume of hydrogen that may be generated exhibits a carbon intensity score less than 0.45 kg $CO_{2eq}$/kg $H_2$.

In some embodiments, the techniques described herein relate to a method, wherein the hydrogen quantification operation includes determining the $Fe^{2+}/Fe^{3+}$ ratio within geologic formations, and the hydrogen produced has a carbon intensity score of less than 1.5 kg $CO_{2eq}$/kg $H_2$. In some embodiments, the method further includes measuring an abundance of $Fe^{2+}$ in the geological sample. In some aspects, the method further includes measuring a proportion of $Fe^{2+}$ to $Fe^{3+}$. In some aspects, the hydrogen production is quantified based on the proportion of $Fe^{2+}$ to $Fe^{3+}$.

In some aspects, a potential for carbon mineralization or a sulfur mineralization is quantified based on the proportion of $Fe^{2+}$ to $Fe^{3+}$. In some aspects, the proportion of $Fe^{2+}$ to $Fe^{3+}$ is measured using spectroscopy. In some aspects, the method further includes quantifying a potential volume of hydrogen that may be generated, wherein the potential volume is quantified based on the proportion of $Fe^{2+}$ to $Fe^{3+}$.

In some aspects, the hydrogen produced exhibits a carbon intensity score less than 3.0 kg $CO_{2eq}$/kg $H_2$. In some aspects, the hydrogen produced exhibits a carbon intensity score less than 1.5 kg $CO_{2eq}$/kg $H_2$. In some aspects, the hydrogen produced exhibits a carbon intensity score less than 0.45 kg $CO_{2eq}$/kg $H_2$.

In further aspects, an analytical instrumentation system for evaluating hydrogen generation potential from a geological source rock is provided. The analytical instrumentation system includes sample containers configured to contain a geological sample of the geological source rock and analytical instrumentation configured to determine one or more properties of iron in the geological sample. The analytical instrumentation includes a Mössbauer spectrometer configured to measure an abundance of $Fe^{3+}$ and an abundance of $Fe^{2+}$ in the geological sample and a computing device. The computing device includes a processor and memory storage operably coupled to the processor. The memory storage hosts one or more computer programming routines, and the processor is configured to read and execute the one or more computer programming routines. The one or more computer programming routines include machine readable and executable instructions to: determine one or more properties of iron in the geological sample; and perform a hydrogen quantification operation based on the one or more properties of iron to determine a potential for hydrogen production without injection of a reactant.

In some embodiments, the techniques described herein relate to a method for evaluating hydrogen generation potential from a geological source rock. The method includes: obtaining a geological sample of the geological source rock; determining a mineralogy of the geological sample; and quantifying a volume of hydrogen generation from the geological source rock based on the mineralogy, wherein the hydrogen is generated without injection of a reactant.

In some embodiments, the step of determining the mineralogy of the geological sample includes one of: i. using x-ray diffraction, scanning electron microscope-energy dispersive X-ray spectroscopy, or optical mineralogy, ii. measuring an abundance of minerals with $Fe^{2+}$, directly measuring an iron content using x-ray fluorescence, neutron activation, Inductively Coupled Plasma Mass Spectrometry (ICP-MS), and Inductively Coupled Plasma Optical Emission Spectrometry (ICP-OES) of the geological sample, and apportioning the iron content between the minerals with $Fe^{2+}$; iii. measuring an abundance of minerals with $Fe^{2+}$, separating the minerals with $Fe^{2+}$, and directly measuring an iron content of individual phases of minerals without $Fe^{2+}$; or iv. using Mössbauer spectroscopy to directly measure $Fe^{3+}$ and $Fe^{2+}$ in the geological sample combined with directly measuring an iron content using x-ray fluorescence, neutron activation, ICP-MS, or ICP-OES.

In some aspects, the hydrogen generation includes a volume of hydrogen generated over geologic time or a potential volume of hydrogen that may be generated. In other aspects, the mineralogy includes primary minerals $H_1$ capable of generating hydrogen. In some aspects, the primary minerals $H_1$ includes one or more minerals selected from the group of olivine, pyroxene, orthopyroxene, clinopyroxene, oxides, spinels, amphiboles, garnets, inosilicates, or sorosilicates. In some aspects, the mineralogy includes secondary minerals $H_2$ that previously generated hydrogen.

In some aspects, the secondary minerals $H_2$ includes one or more minerals selected from a group of chlorite, hematite, magnetite, lizardite, and biotite.

In some aspects, the secondary minerals $H_2$ includes a subset $H_{2a}$ of minerals capable of generating hydrogen. In some aspects, the subset $H_{2a}$ includes magnetite, antigorite, chrysotile, cronstedtite, brucite, lizardite, chlorite, smectite, vermiculite, carbonates (siderite), chromite, ulvospinel, hercynite, magnesioferrite, zeolites, prehnite, and pumpellyite.

In other aspects, the secondary minerals $H_2$ include a subset $H_{2b}$ of minerals incapable of generating further hydrogen. In some aspects, the subset H2b includes one or more minerals selected from the group of hematite, goethite, maghemite, celadonite/glauconite, kaolinite, epidote, and garnets.

In some aspects, the mineralogy includes one or more minerals $H_0$ unrelated to hydrogen generation. In some aspects, the one or more minerals $H_0$ includes quartz, plagioclase, calcite, and gypsum.

In some embodiments, the mineralogy is determined by modal mineralogy. In some embodiments, the method further includes developing a natural hydrogen source rock modal mineralogy model. In some aspects, a natural hydrogen source rock modal mineralogy model indicates source rock quality at various scales.

In some aspects, the mineralogy includes one or more of: primary minerals $H_1$ involved in hydrogen generation; secondary minerals $H_2$ that previously generated hydrogen, wherein the secondary minerals $H_2$ include a subset $H_2a$ of minerals capable of further generating hydrogen and a subset $H_{2b}$ of minerals incapable of generating hydrogen; and one or more minerals $H_0$ unrelated to hydrogen generation.

In some aspects, the geological sample has a Source Rock Maturity (SRM) greater than 8% as defined herein. In other aspects, the step of determining the mineralogy includes scanning electron microscopy with energy dispersive x-ray spectroscopy detectors to measure mineral phases, and further including developing mineral maps of the geologic samples illustrating source rock maturity of a plurality of geological source rock.

In some aspects, the geological sample has a Source Rock Potential (SRP) greater than 0.5%, wherein the SRP is defined herein. In some aspects, the techniques described herein relate to a method, further including calculating a ratio of SRM:SRP to evaluate hydrogen source rock components.

In some aspects, a Hydrogen Source Relevance (HSR) of the geological sample is quantified according to an equation defined herein. In other aspects, the Hydrogen Source Relevance is calculated for a geological sample that exhibits a $H_2/H_1 > 0.04$ and a [Fe] greater than 4%.

In some aspects, the method further includes quantifying the hydrogen generation based on the HSR. In some aspects, the techniques described herein relate to a method, further including utilizing the geological source rock for natural hydrogen exploration. In some aspects, the techniques described herein relate to a method, further including evaluating hydrogen source rock components based on the HSR. In some aspects, the techniques described herein relate to a method, further including the step of determining a magnetic susceptibility of the geological sample.

In some aspects, the method further includes categorizing the geological source rock according to categories, the categories including: elevated abundances of $H_1$ minerals indicate a target geological source rock for hydrogen generation via stimulation processes, elevated abundances of $H_2$ minerals indicate a target geological source rock for conventional or unconventional hydrogen exploration, and elevated abundances of $H_0$ minerals indicate a source rock with low potential for hydrogen exploration.

In some aspects, the step of quantifying the hydrogen generation includes normative mineralogy calculations to determine proportions of the $H_0$ and $H_1$ minerals of the geological sample. In some aspects, the normative mineralogy calculations are based on oxide data. In some aspects, the oxide data is received from a public or a proprietary database. In some aspects, the normative mineralogy calculations include CIPW calculations.

In some aspects, the hydrogen generation is calculated using the mineralogy according to an equation M1 calculated for each mineral: where $m_{rock}$ is the mass of sample being analyzed, $\mu_i$ is the relative abundance of mineral i in the sample, $X_i$ is an iron concentration of each mineral i, $MW_i$ is the molecular weight of mineral i in kg/mol, and $\sigma_i$ is the stoichiometric ratio of moles of hydrogen generated from moles of mineral i, and wherein the equation $M_1$ is calculated for each mineral of the geological sample.

In some aspects, the techniques described herein relate to a method, wherein the hydrogen generation is calculated using the mineralogy according to an equation $M_1$ calculated for each mineral: where $m_{rock}$ is the mass of sample being analyzed, $\mu_i$ is the relative abundance of mineral i in the sample, $X_i$ is an iron concentration of each mineral i, Yi is a ratio of Fe2+/Fetotal of iron of each mineral i, MWi is the molecular weight of mineral i in kg/mol, and $\sigma_i$ is the stoichiometric ratio of moles of hydrogen generated from moles of mineral i, and wherein the equation $M_1$ is calculated for each $H_1$ and $H_{2a}$ mineral of the geological sample.

In some aspects, the techniques described herein relate to a method, wherein the hydrogen generation is calculated using the mineralogy according to an equation $M_1$ calculated for each mineral: where $m_{rock}$ is the mass of sample being analyzed, $\mu_i$ is the relative abundance of mineral i in the sample, ki is a kinetic factor indicative of a speed at which the alteration reaction proceeds, $X_i$ is an iron concentration of each mineral i, $Y_i$ is a ratio of $Fe^{2+}/Fe_{total}$ of iron of each mineral i, $MW_i$ is the molecular weight of mineral i in kg/mol, and oi is the stoichiometric ratio of moles of hydrogen generated from moles of mineral i, and wherein the equation $M_1$ is calculated for each $H_1$ and $H_{2a}$ mineral of the geological sample.

In some aspects, the techniques described herein relate to a method, wherein an estimated quantity of moles of hydrogen previously generated is calculated using the mineralogy according to an equation M2 calculated for each mineral: wherein $m_{rock}$ is the mass of sample being analyzed, $\mu_i$ is the relative abundance of mineral i in the sample, $X^i$ is an iron concentration of each mineral i, Zi is the ratio of $Fe^{3+}/Fe_{total}$ of iron in mineral i, $MW_i$ is the molecular weight of mineral i in kg/mol, and oi is the stoichiometric ratio of moles of hydrogen generated from moles of mineral i, and wherein the equation $M_2$ is calculated for each $H_2a$ and $H_{2b}$ mineral of the geological sample.

In some aspects, the method further includes evaluating hydrogen source rock components based on the estimated quantity of moles of hydrogen generated per unit rock. In some aspects, the method further includes storing the mineralogy and calculated hydrogen generation in a database. In some aspects, the techniques described herein relate to a method, further including obtaining a plurality of geological samples, determining mineralogies of the plurality of geological samples, and mapping a distribution of the mineralogies. In some aspects, the distribution includes rocks of similar mineralogies. In some aspects, mineralogy similarity is based on oxide data and a reaction with an acidic solution. In some aspects, the acidic solution includes hydrochloric acid.

In some aspects, mapping the distribution includes receiving and incorporating geophysical data into the distribution, wherein the geophysical data includes airborne gravity measurements, magnetic measurements, 2D/3D seismic measurements, and airborne gravity and magnetics. In some aspects, the method further includes extrapolating zones of interest or target intervals and depths of geologic hydrogen exploration. In some aspects, the step of obtaining the geological sample includes obtaining drill cuttings collected from a borehole or from a sample repository.

In some aspects, a method for evaluating hydrogen generation potential from a geological source rock is provided. The method includes: obtaining a geological sample of the geological source rock; determining oxide data and carbonate reactivity of the geological sample, wherein the oxide data includes one or more of iron, magnesium, and silica data; and utilizing the geological source rock for hydrogen exploration based on evaluating the oxide data and the carbonate reactivity, wherein hydrogen is generated without injection of a reactant.

In some aspects, the oxide data includes an iron content, a magnesium content, and a silica content. In some aspects, the iron content is greater than about 4%, the magnesium content is greater than about 4%, the silica content is less than 60%, and oxide data is calculated as a percentage of a weight of oxide present in the geological sample compared to a total weight of the geological sample. In some aspects, the carbonate reactivity is determined by calculating a volume of carbon dioxide released when the geological sample reacts with an acidic solution. In some aspects, the acidic solution includes hydrochloric acid. In some aspects, the geological source rock includes a natural hydrogen exploration target if a reaction with the acidic solution occurs for at least 7% of the rock volume.

In some aspects, the method further includes identifying a geological source rock capable of producing hydrogen exhibiting a carbon intensity score of less than 3.0 kg $CO_{2eq}$/kg $H_2$, preferably less than 1.5 kg $CO_{2eq}$/kg $H_2$, and most preferably less than 0.45 kg $CO_{2eq}$/kg $H_2$.

In some embodiments, a method for evaluating hydrogen generation potential from a geological source rock is provided. The method includes: obtaining oxide data and carbonate reactivity for one or more geological source rocks from a database, wherein the oxide data includes iron, magnesium, and silica data; determining iron content of the iron data, magnesium content of the magnesium data, and silica content of the silica data; and utilizing the geological source rock for hydrogen exploration based on evaluating the oxide data and the carbonate reactivity, wherein hydrogen is generated without injection of a reactant.

In some aspects, the iron content is greater than about 4%, the magnesium content is greater than about 4%, the silica content is less than 60%, and oxide content is calculated as a percentage of a weight of oxide present in the geological sample compared to a total weight of the geological sample. In other aspects, the carbonate reactivity is determined by calculating a volume of carbon dioxide released when the geological sample reacts with an acidic solution. In still further aspects, the acidic solution includes hydrochloric acid. In some aspects, the geological source rock includes a natural hydrogen exploration target if a reaction with the acidic solution occurs for at least 7% of the rock volume. In some aspects, the database of oxide data is publicly accessible.

In some aspects, the techniques described herein relate to a method, further including identifying a geological source rock capable of producing hydrogen exhibiting a carbon intensity score of less than 3.0 kg $CO_{2eq}$/kg $H_2$, less than 1.5 kg $CO_{2eq}$/kg $H_2$, or less than 0.45 kg $CO_{2eq}$/kg $H_2$.

In some aspects, a method for evaluating hydrogen generation potential from a geological source rock, wherein hydrogen is generated without injection of a reactant, is provided. The method includes: obtaining a geological sample of the geological source rock; determining a density of the geological sample; determining a coloration of the geological sample; and determining a quality of the geological sample based on the density and the coloration.

In some aspects, the step of determining the density includes measuring a mass of the geological sample, submerging the geological sample in water to determine an associated displaced volume, and calculating the density. In other aspects, determining the coloration includes analyzing a plurality of pixels of a digital image of mineral cuttings of the geological sample to generate one or more intensity values. In some aspects, each intensity value is provided for a color selected from a group of blue, green, and red.

In some aspects, the coloration is defined by each color having an intensity value above a threshold intensity for the plurality of pixels. In some aspects, the coloration is defined by each color having an intensity value above a threshold intensity for a minimum number of pixels. In some aspects, each of the intensity values of red and green are greater than the threshold intensity for at least 40% of the individual pixels, and wherein the density is greater than 2.72 g/cm$^3$ or less than 2.5 g/cm$^3$. In some aspects, the techniques described herein relate to a method, wherein the geological sample corresponds to olivine-, hematite-, or magnetite-rich rock.

In some aspects, the method further includes evaluating hydrogen source rock components by determining a magnetic property, wherein the magnetic property and the coloration are indicative of alteration characteristics. In some aspects, evaluating hydrogen source rock components includes determining a color variation, wherein the color variation and the coloration are indicative of alteration characteristics.

In some aspects, the method further includes identifying a geological hydrogen source rock capable of producing hydrogen exhibiting a carbon intensity score of less than 3.0 kg $CO_{2eq}$/kg $H_2$. In some aspects, the carbon intensity score is less than 1.5 kg $CO_{2eq}$/kg $H_2$. In some aspects, the carbon intensity score is less than 0.45 kg $CO_{2eq}$/kg $H_2$.

Features from any of the disclosed embodiments may be used in combination with one another, without limitation. In addition, other features and advantages of the present disclosure will become apparent to those of ordinary skill in the art through consideration of the following detailed description and the accompanying drawings.

The foregoing brief summary is provided merely for the purpose of summarizing some example embodiments described herein. Because the above-described embodiments are merely examples, they should not be construed to narrow the scope of this disclosure in any way. It will be appreciated that the scope of the present disclosure encompasses many potential embodiments in addition to those summarized above, some of which will be described in further detail below.

BRIEF DESCRIPTION OF THE FIGURES

The drawings illustrate several embodiments of the disclosure, wherein identical reference numerals refer to identical or similar elements or features in different views or embodiments shown in the drawings.

FIG. 1 is a table of stoichiometrically balanced hydrogen generation reactions featuring fayalite and ferrosilite.

FIG. 3 is a table describing the $H_0$, $H_1$, and $H_2$ mineral assemblages and providing example minerals for each category.

FIG. 6 is a table providing the names and chemical formulas for the mineral assemblages associated with $H_1$ and $H_2$a and $H_2$b. Asterisks in the Fe/Mg and $Fe^{2+}$/$Fe^{3+}$ columns indicate that elemental and oxidation states need to be considered in stoichiometric predictions for those minerals.

FIG. 11 is a table describing the generic scenarios associated with the Hydrogen Alteration Index (HAI) results and relating them to hydrogen source rock evaluation.

DETAILED DESCRIPTION

Figure 2:
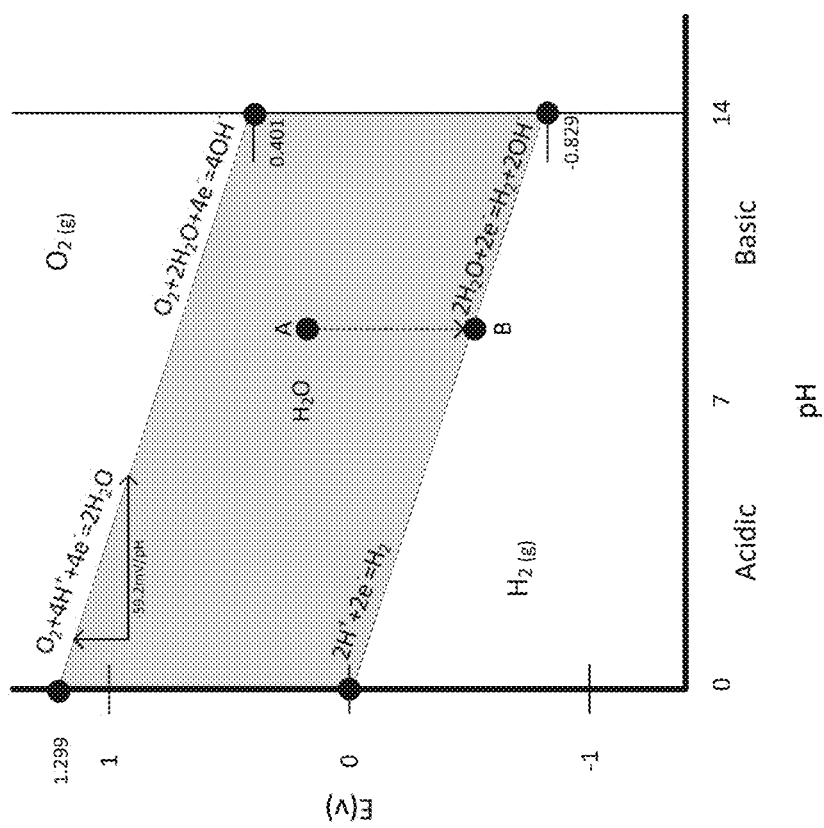
FIG. 2 is a Pourbaix diagram showing the water stability field based on Eh-pH values.

Embodiments of the present disclosure relate generally to the field of energy extraction, geology, geochemistry, mineralogy, geologic hydrogen extraction, subsurface geologic hydrogen stimulation, or subsurface carbon sequestration by carbon mineralization or sulfur sequestration by sulfur mineralization. Measurements of the elemental or oxide content of a rock can provide estimates of its idealized mineralogy based on a series of geochemical rules and calculations. In other embodiments, source rock mineralogy is used to classify portions of the rock into altered minerals that have previously released hydrogen during their formation, unaltered minerals that can potentially generate more hydrogen through alteration processes, and minerals that are unrelated to hydrogen generation. The present specification focuses on systems and methods involved in the analysis of geochemical characteristics of geologic materials, and the systems and methods involved in the utilization of these data for improved geologic hydrogen exploration.

Although the present specification focuses on hydrogen exploration, it is understood that the techniques disclosed herein are not so limited and find application in the drilling for a variety of naturally occurring molecules, including hydrogen, dihydrogen sulfide, hydrogen derivatives, helium, other noble gases, hydrocarbons, nitrogen, and carbon dioxide. It is also understood that these techniques may include the stimulation and in situ generation or release of hydrogen or other hydrogen derivatives (e.g., enhanced hydrogen production (EHP)), the stimulation and in situ generation of hydrogen and simultaneous sequestration of carbon dioxide, dihydrogen sulfide (sulfur enhanced hydrogen production or SEHP), or combinations thereof (sulfur and carbon dioxide-sulfur mixtures enhanced hydrogen production or SCMEHP) (see [Eymold et al., 2024]), and the production, purification, or handling of those fluids, drilling for the recovery of other natural subsurface resources (e.g., geothermal heat, minerals/ores, groundwater), and the production, purification, or handling of those resources, drilling for the purpose of subsurface sequestration of fluids (e.g., carbon dioxide, dihydrogen sulfide), gas storage (e.g., hydrocarbons, hydrogen, or helium), brine or wastewater disposal, enhanced geothermal, and other types of drilling into the subsurface where fluids may be detected, monitored, or quantified.

As used herein, and unless the context dictates otherwise, the following terms have the meanings as specified below.

The term "geologic hydrogen" generally refers to hydrogen produced from a subsurface geological formation.

The term "geologic hydrogen source" generally refers to hydrogen sourced from any subsurface formations via a wellhead connected to a wellbore or any other pathway from the subsurface to the surface by which geologic hydrogen may be transmitted. Notably, this definition includes hydrogen generated by various mechanisms and chemical mixtures, including hydrogen produced by inorganic (e.g., redox, serpentinization) or radioactive processes. For example, a geologic hydrogen source includes hydrogen produced from a geological formation or accumulations, e.g. at young oceanic crust near a mid-oceanic ridge, continental rift, or other reduced iron deposit (e.g., banded iron formation [BIFs]). Geologic formations may include a variety of rock deposits containing complex mixtures or layers of reduced iron mineral phases or organic matter. For example, geologic formations that are suitable for providing a hydrogen feedstock include robust deposits of mafic and ultramafic igneous rock including olivine- and pyroxene-bearing ores. Rock deposits yield abiotic hydrogen through the reaction of water with the rock deposits to mineralize oxygen and release hydrogen. Other organic-rich rock deposits and fluids can undergo pyrolysis and generate hydrogen during graphitization and/or coalification.

Importance of Source Rock Evaluation in Geologic Hydrogen Systems Analysis

Hydrogen systems exploration workflows involve the identification and mapping of suitable quality natural hydrogen source rocks that contain elevated proportions of both unaltered (primary) and altered (secondary) minerals involved in the generation of hydrogen. Notably, an important aspect of natural hydrogen exploration involves determining the parts of basins, blocks, or other geologic/geographic features that contain the highest quality source rocks (i.e., locations with the highest rates of hydrogen generation on a moles of hydrogen per mass or volume of rock basis or "sweet spots").

Identifying the optimal locations to find hydrogen generating source rocks depends upon the exploration strategy. "Conventional" exploration seeks to identify natural hydrogen that formed and migrated to and accumulated within reservoir rocks contained by lithological seals with suitable trapping geometries. By comparison, "unconventional" exploration seeks to identify natural hydrogen that formed and charged source-reservoir systems and is dominantly contained within mature source rocks. Either exploration pathway requires the rigorous identification of mature source rocks that have generated significant volumes of hydrogen, with a priority on quantifying optimal zones of hydrogen generation and allowing for quantitative assessment of the relative volumes of hydrogen generation with respect to the size of prospective reservoirs. Further, both conventional and unconventional are referred to as natural hydrogen generation, meaning hydrogen production or generation that occurs without the injection of a reactant or stimulant into a geological source rock.

Alternatively, identification of exploration targets for enhanced hydrogen production (EHP) or associated carbon or sulfur mineralization requires identification of source rocks with high proportions of mineral species that have not yet been altered (e.g., olivines, pyroxenes) and are capable of generating hydrogen. Similarly, these lithologies with unaltered minerals that can be targets for hydrogen generation may also be targets for the sequestration of carbon, sulfur, or both. In contrast to natural hydrogen exploration or production, enhanced hydrogen production (EHP) requires the injection of a reactant or stimulant into a geological source rock for hydrogen production or generation.

"Conventional" natural hydrogen exploration processes necessitate the identification of high-quality source rocks that have generated significant volumes of hydrogen that would have migrated through subsurface formations and potentially accumulated within reservoirs that are contained within structural or stratigraphic traps and sealed by a low permeability lithology that impedes further buoyant flow. In that scenario, an ideal natural hydrogen source rock will have a high initial proportion of primary minerals involved in hydrogen generation without an abundance of other unrelated minerals and have a present mineralogy dominated by altered mineral phases that have already generated hydrogen during the alteration process. As a result, a method to score and rank high-quality source rocks for conventional hydrogen exploration is required in order to develop standard exploration workflows for conventional natural hydrogen, such as mapping source rocks, migration pathways, prospective reservoirs, prospective traps, and prospective scaling lithologies. Robust source rock evaluation tools are also required to rank prospective hydrogen systems at various scales, such as globally, within a particular region, within a country, within a basin or system, or even within a borehole.

"Unconventional" natural hydrogen exploration processes necessitate the identification of high-quality source rocks that have generated significant volumes of hydrogen and either have accumulated hydrogen within source rock-reservoirs or are actively generating hydrogen at economic rates and volumes. Exploration for source rock-reservoirs is in some ways analogous to exploration for shales that are both source rocks and serve as unconventional reservoirs for methane extraction. As a result, a method to score and rank high-quality source rocks for unconventional hydrogen exploration is required in order to identify specific targets for unconventional natural hydrogen exploration in these settings. Robust source rock evaluation tools are also required to rank prospective unconventional hydrogen systems at various scales, such as globally, within a particular region, within a country, within a basin or system, or even within a borehole.

The methods described above and below detail the processes to determine hydrogen generation capability of a given rock sample and place that data into the context of how these methods can be used to evaluate, rank, and high-grade the source rock components of natural hydrogen systems.

In the typical oil and gas exploration workflow, source rocks are evaluated to determine maturity, or the proportion of source rock that has already generated hydrogen. Methods that do this can include determining the vitrinite reflectance (Ro), the conodont alteration index (CAI), or using Rock-Eval® pyrolysis. In recent decades, the latter has become the standard practice for source rock evaluation. The Rock-Eval process involves measuring various rock and fluid properties, including three distinct measurements: S1 (measurement of free hydrocarbons available in the rock), S2 (volume of hydrocarbons formed during thermal pyrolysis), and S3 (CO2 released during thermal destruction of kerogen). Using Rock-Eval, the source rock potential of a sample of petroleum source rocks can be estimated by comparing S1 and S2 to determine past and future hydrocarbon generation potential or to develop conceptual or geologic models of where to explore for hydrocarbons in other parts of basins or in other basins, or to confirm that samples were collected from within an active hydrocarbon system.

The Rock-Eval process developed for petroleum systems does not conceive of or consider key aspects of the natural hydrogen generation process, including methods, systems, or data acquisition and processing requirements to properly investigate the generation of hydrogen over geologic time or the potential for future hydrogen generation. The background, methods and embodiments disclosed below document a series of novel methods to evaluate source rock quality for natural hydrogen systems and develops the capability to categorize, rank, and high-grade natural hydrogen source rocks for a variety of exploration approaches. Specifically, the newly developed methods for evaluating hydrogen source rocks disclosed herein can be used to identify and prioritize targets for natural hydrogen exploration and differentiate those targets from source rocks suitable for EHP alone or systems in which a combination of natural hydrogen exploration and EHP targets coexist.

Geologic Hydrogen Generation and Source Rocks

The most prevalent high-quality source rock for natural hydrogen systems consists of iron-rich rock, iron-rich mafic or ultramafic rock (e.g., basalt, gabbro, diabase, peridotite, dolerite, dunite) with large proportions of iron in the reduced form ($Fe^{2+}$, or less commonly $Fe^0$), or other rocks with large proportions of minerals containing iron in the reduced form ($Fe^{2+}$, or less commonly $Fe^0$), including metamorphosed or hydrothermally altered mafic or ultramafic igneous rock, olivine- or pyroxene-bearing metamorphic or sedimentary rock or sediment, metamorphosed or hydrothermally altered olivine- or pyroxene-bearing metamorphic or sedimentary rock or sediment, serpentine mineral-bearing rock or sediment, partially or completely serpentinized rock, serpentinite, eclogites, prehnite-pumpellyites, amphibole-rich igneous or metamorphic rock, amphibolite, pyrite-bearing rock, or an iron-rich or other metalliferous ore deposit.

As these natural hydrogen source rocks undergo alteration through water-rock interactions, hydration, hydrothermal alteration, or metamorphism, the reduced forms of ferrous iron ($Fe^{2+}$), or less commonly metallic iron ($Fe^0$), contained in various iron-rich mineral assemblages are oxidized to ferric iron ($Fe^{3+}$) and behave as an electron donor that can react with other chemical species in the subsurface. In most instances, the ferric iron ($Fe^{3+}$) generated by these processes is incorporated into secondary mineral products resulting from the alteration processes described above.

In a variety of subsurface environments, the free electron created by this process (e.g., during serpentinization) can interact with and reduce water (i.e., lower the oxygen fugacity) and produce hydrogen gas according to idealized reactions shown in (FIG. 1). This process of electron transfer and the reduction of water to form hydrogen is graphically represented in a cross plot of oxygen fugacity (E (v), sometimes called Eh or oxygen fugacity) versus pH (FIG. 2); this graph is commonly referred to as the stability field of water in natural environments (e.g., Pourbaix diagram).

The conditions in which mineral hydration alteration reactions capable of generating hydrogen are controlled by the molar abundance of various reduced forms of iron or other redox sensitive elements (e.g., Mn, Cr) and limited availability of other free electron acceptors (e.g., $O_2(g)$, $SO_4^{2-}$, $HCO_3^-$) or oxidizing species inside the stability field of water. When pore fluids are depleted in these electron acceptors during the alteration reactions described above, $Fe^{3+}$ will be incorporated into thermodynamically stable (or metastable) mineral phases and water will be reduced to form hydrogen gas ($H_2$). The process is represented by the dashed arrow in FIG. 2. Water with a starting composition of A is increasingly depleted in oxidants, moving down the Y-axis until water is no longer stable in composition B, and any free electrons then reduce water, producing hydrogen.

In addition to variations in pore water chemistry, further complexity stems from the fact that $Fe^{2+}$ may be contained in a variety of different minerals, which have varying degrees of reactivity (i.e., some minerals react quickly, while others have kinetic limitations to alteration). Additionally, the mineral alteration products resulting from the hydration reactions may incorporate variable concentrations of iron with exclusively $Fe^{2+}$, exclusively $Fe^{3+}$, predictable proportions of $Fe^{2+}$ and $Fe^{3+}$, or variable proportions of $Fe^{2+}$ and $Fe^{3+}$. If $Fe^{2+}$ is incorporated into the mineral alteration phase without undergoing oxidization, it will not serve as an electron donor and thus will not catalyze hydrogen generation. Because secondary minerals formed by various reactions may also have varying ratios of $Fe^{3+}/Fe^{2+}$ and degrees of reactivity that have the potential to generate additional hydrogen, it is critical to evaluate the proportion of $Fe^{3+}$ and $Fe^{2+}$ by direct or indirect measures described below.

The alteration products formed by earlier episodes of hydrogen that do contain $Fe^{2+}$ (e.g., magnetite, diopside) may be able to react again and form additional hydrogen or, alternatively, these mineral phases may be fully stable and incapable of forming additional hydrogen. As such, a comprehensive data set that includes bulk elemental composition (often expressed as major oxides), mineral assemblage (i.e., relative proportions of each mineral in a given rock, also termed "modal mineralogy"), the iron content of each iron-bearing mineral phase, and the oxidation state of that iron in each mineral phase (i.e., $Fe^{3+}/Fe_{total}$ or $Fe^{2+}/Fe_{total}$) is needed to fully quantitatively evaluate hydrogen source rock.

Classification of Hydrogen Related Mineral Phases

For the purpose of hydrogen source rock evaluation, mineralogy can be classified into three general categories: 1) minerals that can be altered by the reaction described above and below to generate geological hydrogen, 2) minerals indicative of past generation of hydrogen in the system, and 3) minerals that are uninvolved in hydrogen generating reactions. The classification scheme developed for hydrogen-related mineral phases is discussed below and summarized in FIG. 3.

The primary minerals contained in source rocks that are involved in hydrogen generation encompass a broad range of groups and are termed $H_1$. The commonly known $Fe^{2+}$-bearing silicate minerals capable of generating hydrogen include olivine (i.e., forsterite-fayalite: Mg—Fe solid solution series), orthopyroxene (i.e., enstatite-ferrosilite-pigeonite: Ca—Mg—Fe solid solution series), and clinopyroxene (i.e., diopside-hedenbergite-augite: Ca—Mg—Fe solid solution series). Although silicates such as olivine, orthopyroxene, and clinopyroxene are the most common sources for natural hydrogen formation, other mineral phases such as oxides (e.g., magnetite, ilmenite), spinels, amphiboles, garnets, inosilicates, sorosilicates, or others can also contribute to hydrogen generation.

Minerals in the $H_1$ category can be further specified to determine the proportions of mineral types that generate hydrogen, sequester carbon, or sequester sulfur. For example, the mineral olivine ($X_2SiO_4$) where the X cation is a solid solution series between Mg and Fe, where the molar abundance of Mg can react with $CO_2$ to form $MgCO_3$, while the molar abundance of Fe can react with $H_2O$ to form $Fe_3O_4$ and release hydrogen gas or with $H_2S$ to form FeS and release hydrogen gas, each in the presence of the appropriate fluid composition. In summary, the iron endmember can produce hydrogen, oxidize iron, and mineralize sulfur to make sulfides, while the magnesium and carbonate endmembers can produce mineralized carbon to make carbonates during serpentinization processes.

Figure 4:
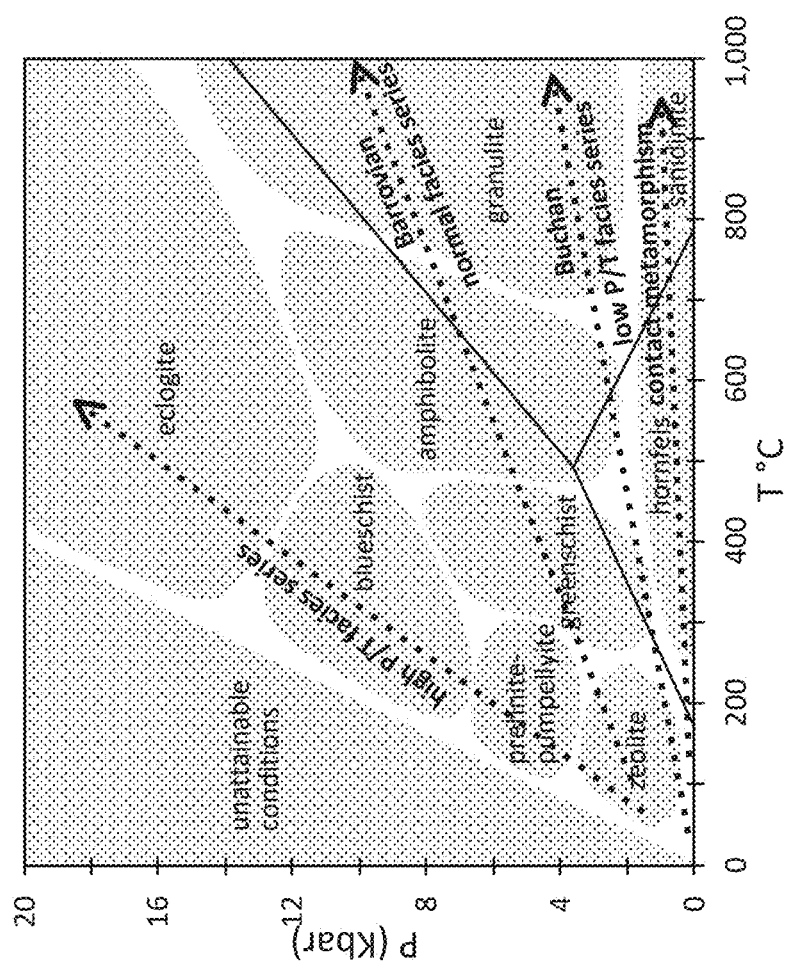
FIG. 4 is a plot of common metamorphic facies (i.e., mineral assemblages formed across various pressure and temperature pathway conditions) documenting the metamorphic evolution of mafic rocks.

Metamorphism of the mineral phases containing high abundances of $Fe^{2+}$ (e.g., minerals contained in mafic rocks) alters the primary minerals into various phases of secondary minerals (collectively referred to as $H_2$ minerals) whose formation is dependent upon the pressure, temperature, and fluid conditions associated with the metamorphic grade and pathways that the mafic rock experiences (FIG. 4). Secondary alteration mineral products that may still retain some degree of $Fe^{2+}$ that can generate additional hydrogen are termed $H_{2a}$ and include antigorite, chrysotile, cronstedtite, brucite, and lizardite), oxides (e.g., hematite and magnetite), and others such as clays with varying degrees of $Fe^{2+}$ (e.g., chlorite, smectite, vermiculite), carbonates (siderite), and spinels (e.g., magnetite, chromite, ulvospinel, hercynite, magnesioferrite) and some low temperature and pressure metamorphic facies (e.g., zeolites, prehnite, pumpellyite). Some of these minerals are a solid solution of magnesium and iron (e.g., olivine is often made up of 85% forsterite (magnesium endmember) and 15% fayalite (iron endmember)). For all these minerals, the generation of hydrogen can be defined on a molar basis which is variable based on iron content, iron oxidation state, and that mineral's degree of reactivity.

Figure 5:
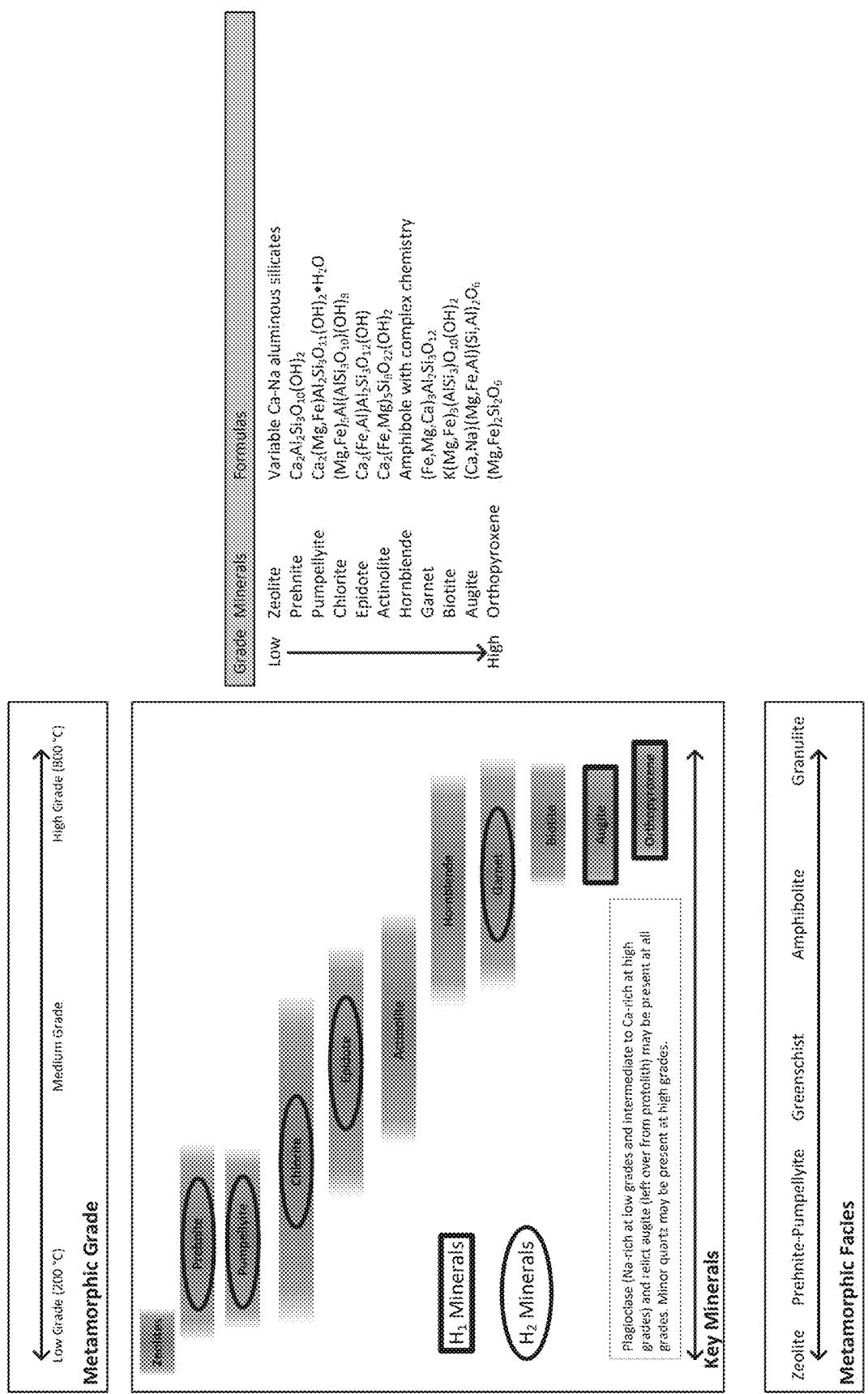
FIG. 5 is a diagram placing the altered minerals in context of the pressure and temperature conditions associated with increasing metamorphic grade, with a table of chemical formulas for each mineral. $H_1$ minerals are outlined by rectangular boxes and $H_2$ minerals are outlined by ovoidal boxes.

Secondary alteration mineral products indicating chemical alteration processes that previously generated hydrogen (i.e., minerals containing $Fe^{3+}$) are termed $H_{2b}$ and include ultramafic alteration products with varying degrees of $Fe^{3+}$ (e.g., antigorite, chrysotile, cronstedtite, brucite, and lizardite), iron oxides (e.g., goethite, hematite, maghemite, magnetite), clays with varying degrees of $Fe^{3+}$ (e.g., celadonite/glauconite, chlorite, kaolinite, smectite), and metamorphic facies with varying degrees of $Fe^{3+}$ (e.g., epidote, garnets, prehnite, pumpellyite). Some of these minerals are associated directly with named metamorphic facies (FIG. 5). For all these minerals, balanced stoichiometric equations using the chemical formulas of these minerals can define past generation of hydrogen on a molar basis which is based on iron content and iron oxidation state (FIG. 5).

In some cases, the exact proportion of $H_{2a}$ and $H_{2b}$ minerals cannot be determined by analyzing the mineralogy alone. Because both of these $H_2$ mineral subsets can contain $Fe^{2+}$ and $Fe^{3+}$, direct quantification of the proportion of each iron valence state and reasonable assumptions may be required to accurately determine the proportion of hydrogen generating minerals between $H_{2a}$ and $H_{2b}$ categories.

Primary minerals that are not directly involved in hydrogen generation are termed $H_0$. Therefore, hydrogen generation associated with a source rock will be dependent on the relative proportions of $H_1$, $H_{2a}$, and $H_{2b}$ minerals, along with considerations of their respective Fe/Mg content and iron oxidation state (FIG. 6).

Methods and systems for hydrogen source rock evaluation are developed here that function similarly to various methods established for petroleum source rock evaluation but are built with the purpose of understanding hydrogen systems and evaluating the quality of geologic hydrogen source rocks. Additionally, the improved estimates of source rock mineralogy and degree of alteration can be correlated to other signals from geophysical surveys or models (e.g., 2D/3D seismic, airborne gravity and magnetics (AGM)) to extrapolate zones of interest and define target intervals and depths as part of geologic hydrogen exploration for conventional or unconventional hydrogen targets. Incorporating geophysical data into the evaluation of hydrogen systems, wherein the geophysical data comprises airborne gravity measurements, magnetic measurements, 2D/3D seismic measurements, and airborne gravity and magnetics, is able to improve hydrogen exploration workflows, particularly in the case of the methods disclosed herein.

Analytical Methods to Evaluate Hydrogen Source Rock

Several embodiments of the current disclosure relate to the methods and systems used to determine the amount of hydrogen generated from prospective hydrogen source rocks. The abundance and reactivity of $Fe^{2+}$ in recently emplaced or unreacted natural hydrogen source rocks can be determined by a variety of methods disclosed herein. Methods for determining the initial proportion of $Fe^{2+}$ include: 1) measuring the abundance of olivine, orthopyroxene, clinopyroxene, and other minerals with reduced $Fe^{2+}$ using laboratory methods (e.g., X-ray diffraction (XRD), scanning electron microscope-energy dispersive X-ray spectroscopy (SEM-EDS), optical mineralogy) and assuming a standard proportion of iron; 2) measuring the abundance of olivine, orthopyroxene, clinopyroxene, and other minerals with reduced $Fe^{2+}$ and directly measuring content of iron and other elements (e.g., by X-ray fluorescence (XRF), neutron activation, Inductively Coupled Plasma Mass Spectrometry (ICP-MS), Inductively Coupled Plasma Optical Emission Spectrometry (ICP-OES)) of the bulk sample and apportioning the iron content between the primary iron-bearing phases, such as olivine, orthopyroxene, clinopyroxene; 3) measuring the abundance of olivine, orthopyroxene, clinopyroxene, and other minerals with reduced $Fe^{2+}$ and directly measuring the iron content of individual mineral phases after separating the primary iron-bearing phases, such as olivine, orthopyroxene, or clinopyroxene; 4) using Mössbauer mass spectrometry to directly measure the $Fe^{3+}/Fe^{2+}$ in a rock sample and combining these iron speciation methods with the alternative methods of measuring the total iron content (e.g., by XRF, neutron activation, ICP-OES, ICP-MS). Below, relevant laboratory analytical methods are described in the context of their application to hydrogen source rock.

Bulk elemental composition of rock samples (e.g., drill cuttings, rock core, or other samples) may be determined using powder XRF, ICP-OES, ICP-MS, Laser Ablation ICP-MS (LA-ICP-MS), Instrumental Neutron Activation Analysis (INAA), or other bulk elemental analysis methods, though the preferred method is XRF, described in detail here.

Prior to XRF analysis, the rock sample is ground to a fine powder using a mortar and pestle, automatic mill, or similar apparatus. This finely ground material is homogenized, which allows for the average bulk elemental composition to be determined. The powder may then be melted into a glass bead, pressed into a pellet, or measured without pelletizing. The sample is then irradiated with high-energy X-rays, which dislodge tightly bound electrons near the nucleus of elements in the sample. Higher energy electrons move in to fill these vacancies, resulting in the emission of characteristic X-rays from the atom, called "fluorescence." These X-rays can be detected by either a wavelength dispersive detector, energy dispersive detector, or similar detector. The intensity of the emitted X-rays is proportional to the concentration of the emitting element in the sample, allowing for quantitative analysis of the major rock forming elements, minor elements, and trace elements present. Data output from this method are in the form of relative elemental abundances of major, minor, and trace rock forming elements (e.g., Si %, Ca %, Mg %, Fc %), which can be numerically converted to relative oxide abundances to be used as inputs in models and normative mineralogy calculations (norms), discussed below. Relevant compositional values used as inputs in calculated norms may include $SiO_2$, $TiO_2$, $Al_2O_3$, $Fe_2O_3$, FeO, MnO, MgO, CaO, $Na_2O$, $K_2O$, $P_2O_5$, or others.

Modal mineralogy (i.e., a quantitative determination of the proportions of the minerals present) of rock samples may be determined using powder diffraction analysis or other analyses (e.g., SEM/EDS, optical mineralogy). The most commonly employed powder diffraction analysis is XRD, but diffraction methods may also be performed using a neutron or electron source in addition to X-rays. Prior to powder diffraction analysis, drilled rock cuttings or core may be ground to a fine powder using a mortar and pestle, automatic mill, or similar apparatus. This finely ground material is then homogenized, which allows for the average bulk mineral content to be determined but destroys mineral texture and mineralogical spatial relationships. The powdered sample is irradiated with monochromatic X-rays, which are diffracted by the crystal lattice of the material, producing a unique diffraction pattern that is characteristic of the atomic structure of the material. Software containing databases of diffraction patterns may then be used to determine the minerals in the rock cuttings or core. Because diffraction patterns are controlled by the atomic structure of the mineral, XRD is capable of characterizing crystalline and sub-crystalline materials but not amorphous (i.e., non-crystalline) material. The process of Rietveld refinement or other refinement methods may analyze pattern intensities and provide the relative proportions of the minerals present in the sample.

High-resolution elemental composition and modal mineralogy of drilled rock cuttings or core may also be determined using scanning electron microscopy in combination with energy dispersive spectroscopy (SEM/EDS). SEM/EDS analysis may be performed on non-powdered drilled rock cuttings, core, thin sections, or other rock and mineral forms, which preserves original texture and mineralogical relationships. A focused high-energy electron beam is directed at a small section of the sample (e.g., micron-scale), which dislodges inner-shell electrons of atoms in the sample, creating vacancies that are filled by higher energy electrons, which emits X-rays characteristic to that element that are measured by the energy dispersive detector.

The EDS system generates a spectrum showing the intensity of X-rays that correspond to different elements, which can be used to calculate their relative abundance. This process may be repeated in a high-resolution grid pattern across the sample, creating a raster-based dataset where each pixel contains full elemental relative abundances that may then be interpreted as rock forming minerals by mineral mapping software. A high-resolution map of elemental composition and full modal mineralogy may then be created and, in some embodiments, superimposed onto the electron micrograph of the geological sample, which also includes two important additional data products not reliably provided by XRD: 1) presence or composition of amorphous mineral phases, and 2) iron content of olivine and pyroxene mineral phases (e.g., accurate determination of an olivine with 80% forsterite and 20% fayalite).

The oxidation state of the iron (i.e., $Fe^{2+}$ or $Fe^{3+}$) is also critical to potential hydrogen generation. Mössbauer spectroscopy may be used to determine the oxidation state of iron in bulk drilled rock cuttings or core, or that of individual minerals separated from drilled rock cuttings or core. As primarily iron-bearing minerals containing $Fe^{2+}$ are altered to secondary minerals and iron is oxidized to $Fe^{3+}$ while reducing water, the oxidized iron is incorporated into a secondary mineral phase. The measurement of the ratio of oxidized iron to the total iron ($Fe^{3+}/Fe_{total}$) of bulk drilled rock cuttings or core, or individual minerals separated from drilled rock cuttings or core, is a key metric used to determine the amount of hydrogen generated and the amount of potential hydrogen remaining in the rock. Prior to Mössbauer analysis, drilled rock cuttings or core may be ground to a fine powder using a mortar and pestle, automatic mill, or similar apparatus. This finely ground material is homogenized, which allows for the average bulk $Fe^{3+}/Fe_{total}$ composition to be determined.

In order to make Mössbauer measurements of $H_2$ minerals, individual minerals in drilled rock cuttings or core may be separated from one another, allowing for mineral-specific measurements of $Fe^{3+}/Fe_{total}$. Mineral separation can occur in distinct ways, several of which are described below. Treatment of powdered samples may involve sieving different grain sizes, as some minerals may be more prevalent in certain size fractions. By floating powdered samples in water, some clays may be removed from the bulk rock. By passing the samples through a series of magnetic fields of different intensities, magnetic minerals may be separated from non-magnetic ones. Minerals have different densities, and heavy liquid separation or a vibrating screen (i.e., a shaker table) may be used to separate minerals based on their specific gravities. Froth flotation methods may be used for separating minerals based on their differential affinities to water. Minerals that are hydrophobic attach to air bubbles and float, while hydrophilic minerals sink. Some minerals are more conductive than others. By applying an electric field, conductive minerals may be separated from non-conductive ones. Under a binocular microscope, minerals can be manually picked based on their color, shape, size, and other physical properties. After mineral separation, individual minerals may be analyzed for $Fe^{3+}/Fe_{total}$ or $Fe^{2+}/Fe_{total}$ to assess the relative contributions of each mineral phase to the overall hydrogen generation of the rock (e.g., on a mole-to-mole basis).

Figure 7:
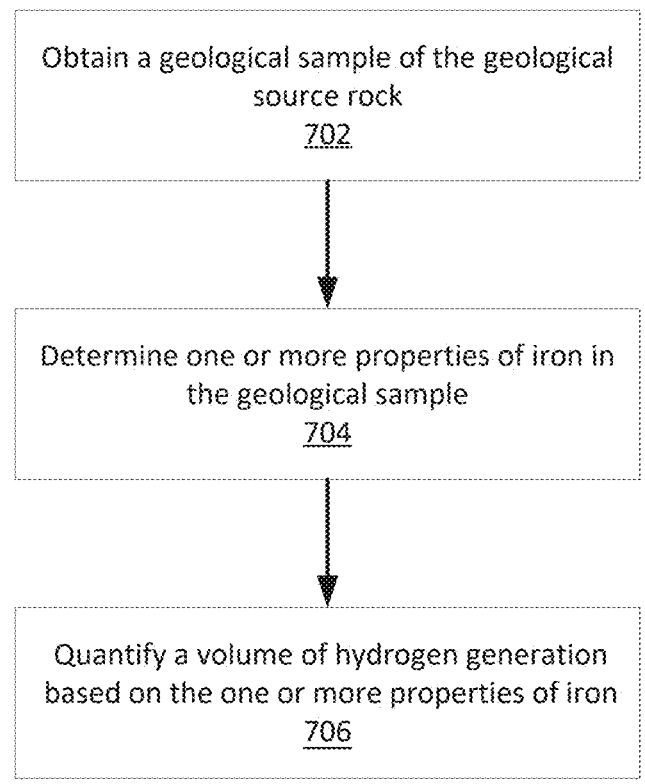
FIG. 7 shows example operations for evaluating hydrogen generation potential from a geological source rock based on iron content of a geological sample, in accordance with some example embodiments described herein.

Looking to FIG. 7, example embodiments are shown for evaluating hydrogen generation potential from a geological source rock via a sample based on one or more properties of iron present in a geological sample. Performance of the method set forth in FIG. 7 will determine one or more properties of the iron present in a geological sample, such as the concentration of iron in a geological or mineral sample or the species of iron in a geological or mineral sample. From these qualities of the sample, the hydrogen generation potential of the geological source rock from which the sample was retrieved is quantified.

As shown in operation 702, the method includes using a drilling apparatus or sample repository to obtain a geological sample. In some embodiments, the geological sample obtained could be obtained from a drilling site in the form of core samples, rock cuttings, or other standard sample varieties. In some embodiments, the geological sample obtained could be obtained from a repository of samples from known locations.

As shown in operation 704, analytical methods are used to determine one or more properties of iron in the geological sample. In some embodiments, the concentration of iron in a rock sample may be determined by first determining the mass of the sample and subsequently subjecting the sample to experimental analysis to determine the iron content of the sample, allowing for the calculation of its iron concentration. In some embodiments, the concentration of iron present in the sample may be quantified as a weight/volume % of iron, the mg/g of iron, a molar concentration of iron, a percentage of the weight of iron oxide present in the sample as compared to the total weight of the geological sample, or any other concentration metric known in the art. In some embodiments, the iron content of the sample may be determined through XRF, SEM/EDS, EDS, ICP-OES, ICP-MS, Laser Ablation ICP-MS (LA-ICP-MS), Instrumental Neutron Activation Analysis (INAA), or other bulk elemental analysis methods. The term "species" of iron in a sample may refer to the identity of the mineral phase the iron is resident to, the molecule the iron atom is a constituent member thereof, or the oxidation state of iron atoms in the mineral phase. In some embodiments, determining the mineral phases present in the geological sample and which contain iron may be accomplished by powder diffraction analysis methods, such as XRD, SEM/EDS, or the like. In some embodiments, the oxidation state of iron atoms in the sample may be determined by Mössbauer spectroscopy or other methods known in the art. In some embodiments, samples may be used as-is for experimentation or may be processed in some way, such as by crushing, comminuting, and/or powdering. In some embodiments, mineral phases of the geological sample may be separated from one another before or after analysis (e.g., by froth flotation methods). In some embodiments, samples may be subjected to one or more forms of analysis before and/or after the samples are processed or subjected to one or more additional analyses.

As shown in operation 706, the data acquired in operation 704 is used to quantify a volume of hydrogen generation based on the one or more properties of iron. In some embodiments, the properties of the iron in the geological sample, as determined in operation 704, may be extrapolated to the geological source rock from which the geological sample was obtained. In some embodiments, extrapolating the iron properties of the geological sample to the geological source rock may comprise assuming a uniform distribution of iron throughout the geological source rock and/or sample which is equivalent to iron content determined for the geological sample. In some embodiments, extrapolating the iron properties of the geological sample to the geological source rock may comprise combining data sets from multiple geological samples collected from different sections of the geological source rock.

In some embodiments, the quantification of the volume of hydrogen generation requires determining a volume of the geological source rock within the region. The volume of the geological source rock may be determined by delineating the extent of the geological source rock formation through sample collection and through geophysical methods (e.g., airborne gravity measurements, magnetic measurements, 2D/3D seismic measurements, and airborne gravity and magnetics). In some embodiments, volumes of subsections of the geological source rock may be calculated and summed to increase the accuracy of volume calculations.

In some embodiments, a first component of the total potential volume of hydrogen generation by a given source rock may be a volume of hydrogen which has already been produced (e.g., over geologic time) by the rock formation as a result of hydrothermal alteration events or other geological processes which have previously occurred to the geological source rock. In some embodiments, a second component of the total potential volume of hydrogen generation by a given source rock may be a volume of hydrogen which may be produced by stimulating the source rock. In some embodiments, quantifying the volume of hydrogen generation may be performed by calculating the $M_1$ or $M_2$ estimates of the geological source rock or sample as described below.

Figure 8:
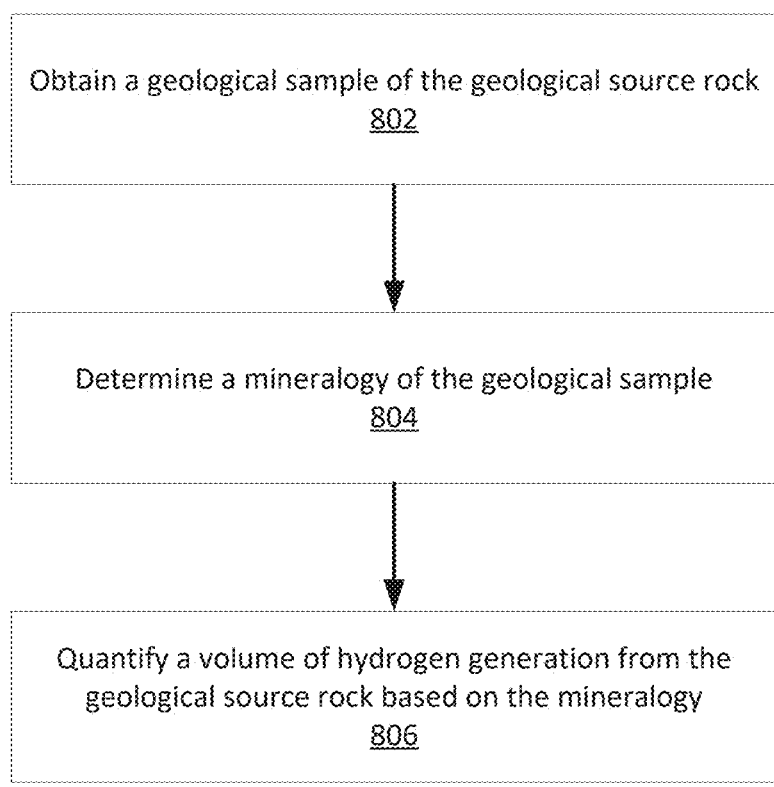
FIG. 8 shows example operations for evaluating hydrogen generation potential from a geological source rock based on the mineralogy of a geological sample, in accordance with some example embodiments described herein.

Turning to FIG. 8, example embodiments are shown for evaluating hydrogen generation potential from a geological source rock. The mineralogy of a source rock may, in many cases, indicate the geologic history of the source rock, including what types of chemical interactions the source rock may have been subjected to previously. The mineralogy can indicate potential future chemical reactions that a geological source rock could undergo, such as its ability to participate in future hydrogen generation.

As shown in operation 802, the method includes using a drilling apparatus or sample repository to obtain a geological sample of the geological source rock. In some embodiments, the geological sample obtained could be obtained from a drilling site in the form of core samples, rock cuttings, or other standard sample varieties known in the art. In some embodiments, the geological sample obtained could be obtained from a repository of samples from known locations.

As shown in operation 804, analytical methods are used to determine a mineralogy of the geological sample. In some embodiments, samples may be used as-is for experimentation or may be processed in some way, such as by crushing, cutting, comminuting, and/or powdering. In some embodiments, mineral phases of the geological sample may be separated from one another before or after analysis. In some embodiments, samples may be subjected to one or more forms of analysis before and/or after the samples are processed or subjected to one or more additional analyses. In some embodiments, the mineralogy of a sample may be determined modally or normatively. In some embodiments, minerals may be further classified as belonging to $H_0$, $H_1$, or $H_2$. In some embodiments, minerals in class $H_2$ may be further classified into sub-classes $H_{2a}$, $H_{2b}$.

As shown in operation 806, the data acquired in operation 804 are used to quantify a volume of hydrogen generation from the geological source rock via a sample based on the mineralogy. In some embodiments, the mineralogy of the sample may be extrapolated to the geological source rock. In some embodiments, the hydrogen generation may have occurred previously, as evidenced by an increased amount of $H_2$ minerals. In some embodiments, the hydrogen generation may be a potential amount of hydrogen which the geological source rock could generate.

Figure 9:
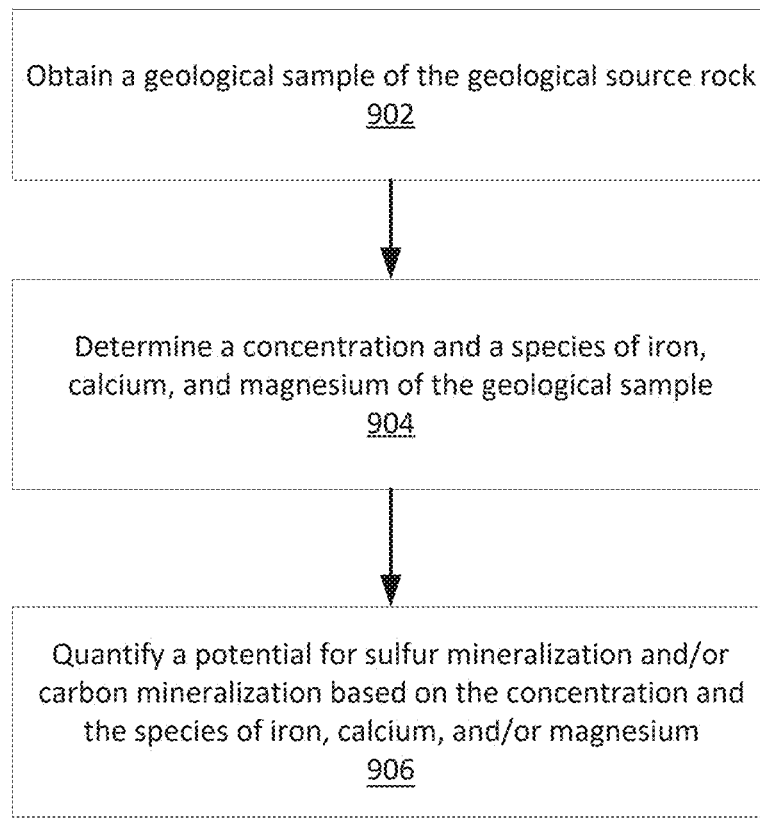
FIG. 9 shows example operations for evaluating carbon and sulfur mineralization potential from a geological source rock based on the mineralogy of a geological sample, in accordance with some example embodiments described herein.

Looking to FIG. 9, example embodiments are shown for evaluating the potential to sequester sulfur and carbon in the geological source rock via the sample. The methods disclosed herein can be used to quantify the concentration of iron, calcium, and/or magnesium in a geological or mineral sample, the species of iron in a geological or mineral sample, and, from these qualities of the sample, quantify a potential for sulfur mineralization and/or carbon mineralization of a sample.

As shown in operation 902, the method includes using a drilling apparatus or sample repository to obtain a geological sample. In some embodiments, the geological sample could be obtained from a drilling site in the form of core samples, rock cuttings, or other standard sample varieties known in the art. In some embodiments, the geological sample obtained could be obtained from a repository of samples from known locations.

As shown in operation 904, analytical methods are used to determine a concentration and a species of iron, calcium, and/or magnesium in the geological sample. In some embodiments, the concentration of iron in a rock sample may be determined by first determining the mass of the sample and subsequently subjecting the sample to experimental conditions which would determine the iron content of the sample, allowing for the calculation of the concentration. In some embodiments, the concentration of the sample may be quantified as a weight/weight % of iron, a weight/volume % of iron, the mg/g of iron, a molar concentration of iron, or any other concentration metric known in the art. In some embodiments, the iron content of the sample may be determined through XRF, SEM/EDS, EDS, ICP-OES, ICP-MS, Laser Ablation ICP-MS (LA-ICP-MS), Instrumental Neutron Activation Analysis (INAA), or other bulk elemental analysis methods. The species of iron, calcium, or magnesium in a sample may be the identity of the mineral phase the iron, calcium, or magnesium is resident to, the molecule the iron, calcium, or magnesium atom is a constituent member thereof, or the oxidation state of iron, calcium, or magnesium atoms in the mineral phase. In some embodiments, determining the mineral phases present in the geological sample and which contain iron may be accomplished by powder diffraction analysis methods, such as XRD, SEM/EDS, or other methods. In some embodiments, the oxidation state of iron atoms in the sample may be determined by Mössbauer spectroscopy or other methods known in the art. In some embodiments, samples may be used as-is for experimentation or may be processed in some way, such as by crushing, comminuting, and/or powdering. In some embodiments, mineral phases of the geological sample may be separated from one another before analysis. In some embodiments, samples may be subjected to one or more forms of analysis before and/or after the samples are processed or subjected to one or more additional analyses.

Figure 10:
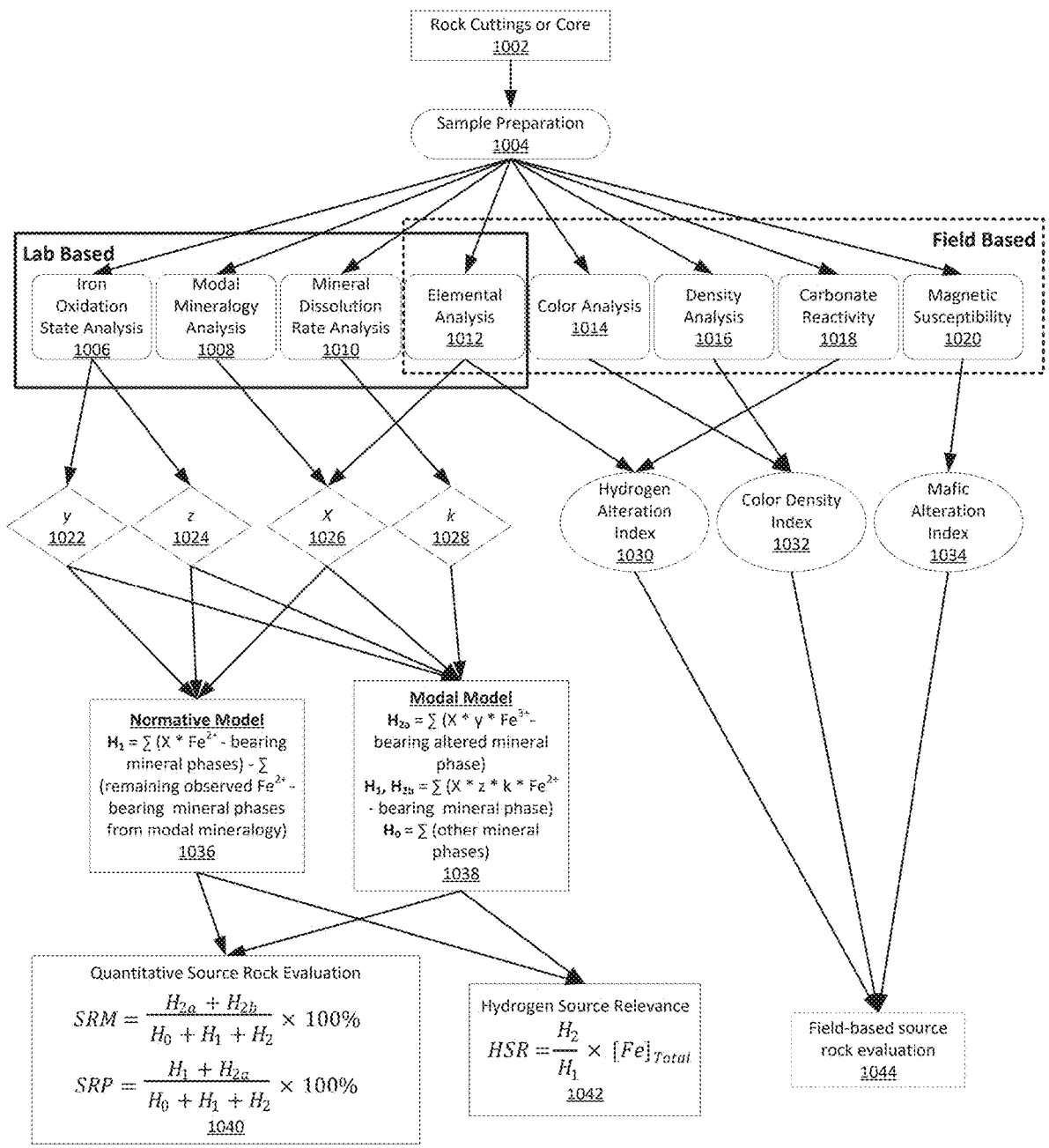
FIG. 10 is a workflow describing an example process for measuring the elemental composition of a rock, determining the normative mineralogy of the sample, assessing iron content of the minerals, and measuring the $H_1$ and $H_2$ mineral assemblages to assess past and future hydrogen generation potential.

As shown in FIG. 10, the techniques above are combined to leverage data with increasing specificity with regards to evaluating hydrogen source rocks by defining $H_0$, $H_1$, and $H_2$ composition in accordance with the availability of increasingly complete datasets. As shown in FIG. 10, samples (e.g., rock cuttings or core 1002) are received, and then sample preparation 1004 may be performed to position the samples for either field-based assessment or lab-based analysis. Field-based assessments 1006-1020 may be performed without physical alteration of the samples during sample preparation 1004. Sample preparation 1004 may comprise crushing, washing, comminuting, powdering, cutting, purifying, isolating, or otherwise altering the samples to prepare them for subsequent assessments/analyses. These field-based assessments may comprise elemental analysis 1012, color analysis 1014, density analysis 1016, carbonate reactivity 1018, and/or magnetic susceptibility 1020. The data resulting from these analyses can be used to estimate various indices of the rock cuttings or core samples 1002, such as the hydrogen alteration index 1030, color-density index 1032, or mafic alteration index 1034 as described herein. All of these data may be used to form a field-based source rock evaluation 1044 which may be used to grade source rocks or estimate the potential of a rock formation as a source of hydrogen.

Laboratory based methods may require physical alteration of the samples during sample preparation 1004. As described above, laboratory-based assessments may comprise iron oxidation state analysis 1006 (e.g., Mössbauer spectroscopy), modal mineralogy analysis 1008 (e.g., powder diffraction), mineral dissolution rate analysis 1010 (e.g., laboratory kinetic experiments), or elemental analysis 1012 (e.g., XRF). From these analyses, several variables may be determined, such as the $Fe^{3+}/Fe_{TOT}$ of the iron endmember of solid solution y 1022, the $Fe^{2+}/Fe_{TOT}$ of the iron endmember of solid solution z 1024, and the fraction of iron endmember of the solid solution X 1026. The dissolution rate of the hydrogen generating mineral phase k 1028 may be determined experimentally using the methods described herein or may be collected from a previously generated data repository. These variables and other data may then be incorporated into a normative model 1036, in order to determine $H_1$, and/or modal model 1038, which in turn enables determination of $H_0$, $H_1$, $H_{2a}$, and $H_{2b}$. Following the establishment of a normative model 1036 and modal model 1038, quantitative source rock evaluation 1040 may be performed in order to calculate the source rock maturity (SRM) and the source rock potential (SRP) as described in greater detail below. Additionally, these models can be used to calculate hydrogen source relevance 1042, as also described below.

Further, identifying the presence of high quality and mature (i.e., rocks that have generated substantial amounts of hydrogen) hydrocarbon source rocks is a necessary component of defining and developing exploration models for petroleum systems. Rock-Eval® pyrolysis described above is a commonly used method for evaluating the presence and quality of hydrocarbon source rocks. The Rock-Eval® process involves measuring various rock and fluid properties, including three distinct measurements: S1 (existing hydrocarbons present in the sample), S2 (remaining hydrocarbon generating potential), and S3 (the proportion of "spent" carbon not related to hydrocarbon generating potential). Using Rock-Eval®, the hydrocarbon source rock potential of a sample can be estimated by comparing S1 and S2 proportions to determine past and future hydrocarbon generation potential of a given petroleum system or to develop conceptual geologic models of where to explore for hydrocarbons in other parts of a geologic province, other geologic provinces, or to confirm that samples were collected from within an active petroleum system. However, Rock-Eval® and other currently available technologies are incapable of measuring key parameters of the geologic hydrogen system, including quantifying the volumes of existing hydrogen or the volumes of hydrogen generated in the geologic past, or evaluating hydrogen source rock potential.

Methods of Evaluating Hydrogen Source Rock Quality
Hydrogen Alteration Index (HAI)

The Hydrogen Alteration Index (HAI) uses oxide data (e.g., from field portable or laboratory-based XRF) together with carbonate reactivity to calculate a modified chemical index of alteration related to past hydrogen generation.

In prior art, the Chemical Index of Alteration (CIA) was developed to provide a measurement of the degree of chemical alteration a rock sample has undergone. This approach is typically utilized to evaluate surface chemical weathering of igneous rocks and is commonly calculated based on the proportions of stable aluminum versus more labile calcium (Ca), sodium (Na) and potassium (K). Here, the CIA is adapted in conjunction with a new alteration metric for prospective hydrogen source rocks.

Bulk quantitative elemental composition generated from drilled rock cuttings or core measured in the field, laboratory, or obtained from public or proprietary databases may be used to determine the CIA of the altered rock. The CIA may be used on subsurface rocks that have been exposed to weathering processes, but also those that occur in response to the circulation of groundwater or hydrothermal fluids. The CIA provides a measure of how altered the igneous rock is relative to its original state. The CIA is calculated using the formula:

$$CIA = \frac{Al_2O_3}{Al_2O_3 + CaO + Na_2O + K_2O} \times 100$$

Here, the oxide units are in moles, and the CaO, $Na_2O$, or $K_2O$ represent the fraction of these oxides in the siliciclastic mineral phases, therefore the CaO represented by the modal abundance of calcite, dolomite, secondary potassium feldspar, or other secondary products are subtracted prior to calculation. High CIA values reflect the removal of labile cations, such as $Ca^{2+}$, $Na^{2+}$, and $K^+$, in relation to the more stable $Al^{3+}$ cation from the rock during chemical alteration. Conversely, low CIA values suggest low weathering effects on these cations. Mafic rocks (i.e., gabbro or basalt) start with a CIA of 0-45. A CIA of 50-60 indicates initial stages of alteration, 60-80 indicates intermediate degrees of alteration, and >80-100 indicates extreme degrees of alteration. While the CIA adequately evaluates the alteration of mafic rocks in surface environments, it does not adequately address hydrogen generating reactions in the subsurface nor identify natural hydrogen targets for conventional or unconventional hydrogen exploration. Therefore, CIA is incapable of determining the moles of hydrogen produced from alteration processes (e.g., serpentinization); this necessitates the development of the hydrogen alteration index (HAI) described below.

The HAI uses one or more of iron, magnesium, silica, and carbonate reactivity to identify suitable hydrogen source rocks and evaluate that rock's level of alteration (and therefore previous hydrogen generation, as compared to remaining hydrogen potential) using data and methods easily executed in the field or laboratory. Mafic and ultramafic rocks (e.g., ferrobasalt, dunite) are examples of quality source rocks for natural hydrogen generation and, as defined by their mineralogy, contain highly elevated amounts of iron and magnesium, with significantly lower silica content than other igneous rocks (e.g., andesite, granite, rhyolite). In addition to these chemical composition requirements, alteration reactions with water or mixed fluids containing water are required to generate hydrogen. In some embodiments, evaluation of hydrogen source rocks (e.g., ferrobasalt, dunite) includes evaluating the starting chemical composition (i.e., elevated iron and magnesium with low silica) in conjunction with an indicator of hydrogen-generating mineral alteration reactions in order to assess hydrogen generation potential and the volumes of previously generated hydrogen, which leads to the identification of hydrogen source rocks and an assessment of their hydrogen maturity.

This embodiment discloses a metric called the HAI that assesses source rock quality and identifies evidence for the alteration reactions that have generated hydrogen. Importantly, this approach can be deployed in the field or the laboratory with an easily acquired and simple dataset. One common component of fluids that interact with mafic rock and produce hydrogen is carbon dioxide, which is precipitated as a carbonate mineral as part of a class of chemical reactions called serpentinization and/or mafic rock metamorphism (FIG. 1). As a result, a cursory evaluation of the degree of mineral alteration related to hydrogen can be determined by quantifying the proportion of the rock that is or was derived from mafic minerals, including $H_1$ and $H_2$ minerals; these components can be determined in the field based on portable XRF analyses. A second step in this process requires evaluating the proportion of the rock sample that exists as carbonate minerals that are indicators of alteration. Acidification by dilute hydrochloric acid (HCl) can liberate carbonate mineral phases, which can be semi-quantitatively evaluated by visual inspection of $CO_2$ degassing or by measuring differences between the masses before and after application of dilute HCl.

The algorithm developed for this process first evaluates key oxide data to determine whether three criteria are met: iron content exceeds an iron content threshold (e.g., [FeO]+ [$Fe_2O_3$]>4%), magnesium content exceeds a magnesium content threshold (e.g., [MgO]>4%), and silica content does not exceed a silica content threshold (e.g., [$SiO_2$]<60%). In some embodiments, the iron content threshold may be 1%, 2%, 3%, 4%, 5%, 6%, 7%, 8%, 9%, or 10% by weight; the magnesium content threshold may be 1%, 2%, 3%, 4%, 5%, 6%, 7%, 8%, 9%, or 10% by weight; and the silica content threshold may be 35%, 40%, 45%, 50%, 55%, 60%, 65%, 70%, 75%, 80%, or 85% by weight. In some embodiments, the percentages of the oxide content are calculated as the proportion of the weight of the oxide to the total weight of the sample. If all three criteria are met, the volume of carbonate released when reacted with HCl is calculated.

This algorithm yields three general scenarios illustrated in FIG. 11. In Scenario 1, the sample can represent a quality hydrogen source rock based on oxide data and exhibit signs of alteration based on reaction with HCl. In Scenario 2, the sample can represent a quality hydrogen source rock based on oxide data but not exhibit signs of alteration based on limited reaction with HCl. In Scenario 3, the sample can represent a poor hydrogen source rock based on oxide data. The results of Scenario 2 suggest the rock has not yet generated significant quantities of geologic hydrogen and could serve as an ideal target for EHP. The results of Scenario 3 suggest the rock has limited capability as a hydrogen source rock for any production strategy. The results of Scenario 1 suggest the rock could serve as a target for conventional or unconventional exploration for natural hydrogen with increasing volumes of previous hydrogen generation (i.e., maturity) indicating greater suitability as a source rock. FIG. 11 provides specific threshold values for each of the mineral content data, although the threshold values may be modified as needed or desired.

Figure 12:
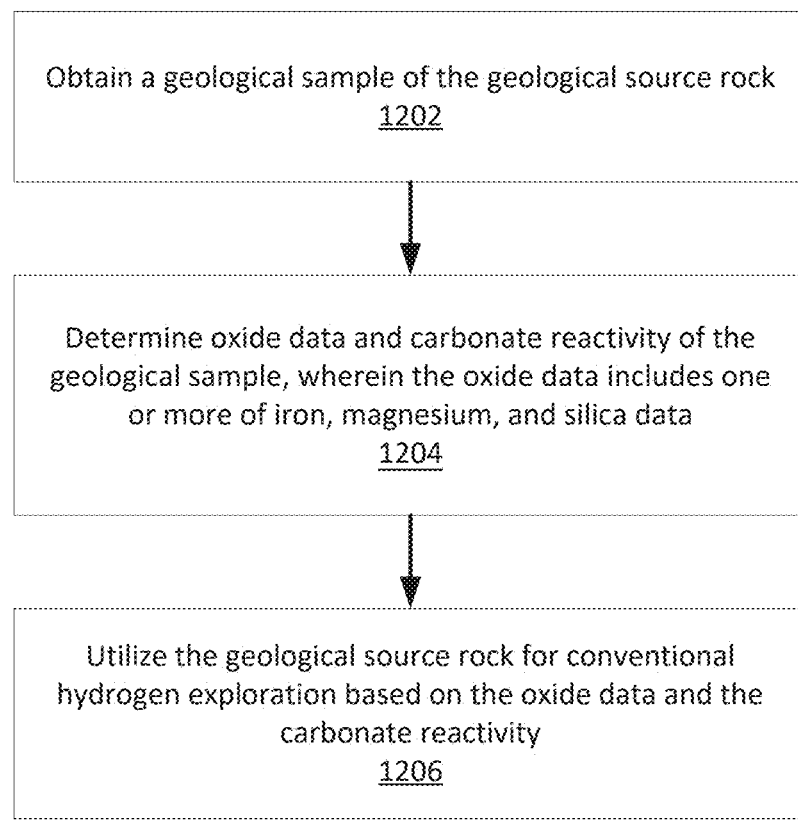
FIG. 12 shows example operations for evaluating hydrogen generation potential from a geological source rock based on the Hydrogen Alteration Index and for natural hydrogen exploration, in accordance with some example embodiments described herein.

Looking now to FIG. 12, example embodiments are shown for evaluating hydrogen generation potential from a geological source rock through analysis of a sample. When searching for a target location in conventional hydrogen exploration, the HAI allows for rapid determination if a geological sample is suitable. As the HAI only requires two main data sets to be collected with field expedient methods, it can be readily employed for geological hydrogen exploration-based tasks.

As shown in operation 1202, the method includes using a drilling apparatus or sample repository to obtain a geological sample of the geological source rock. In some embodiments, the geological sample obtained could be obtained from a drilling site in the form of core samples, rock cuttings, or other standard sample varieties known in the art. In some embodiments, the geological sample obtained could be obtained from a repository of samples from known locations.

As shown in operation 1204, the method includes using analytical methods to determine oxide data and carbonate reactivity of the geological sample, wherein the oxide data includes one or more of iron, magnesium, and silica data. In some embodiments, samples may be used as-is for experimentation or may be processed in some way, such as by crushing, comminuting, and/or powdering. In some embodiments, mineral phases of the geological sample may be separated from one another before or after analysis. In some embodiments, samples may be subjected to one or more forms of analysis before and/or after the samples are processed or subjected to one or more additional analyses. In some embodiments, oxide data can be determined by XRF or other methods known to the art. In some embodiments, the carbonate reactivity may be assessed by reacting the geological sample with a solution containing hydrochloric acid (HCl) or other acid-containing solutions. In some embodiments, the carbonate reactivity may be evaluated by measuring and calculating an amount (e.g. volume, number of moles) of carbon dioxide released when the geological sample reacts with an acidic solution. For example, a release of carbon dioxide greater than 1%, 2%, 3%, 4%, 5%, 6%, 7%, 8%, 9%, 10%, 15%, or 20% is sufficiently significant for determining whether the source rock is suitable for natural or conventional hydrogen generation.

As shown in operation 1206, the geological source rock is then used for conventional hydrogen exploration based on the oxide data and the carbonate reactivity. In some embodiments, determining whether a geological source rock is suitable for natural hydrogen exploration comprises the geological sample having iron content greater than 4%, magnesium content greater than 4%, and silica content less than 60%, and a significant chemical reaction with an acidic solution releasing carbon dioxide (>7% of the rock volume has experienced carbonate mineralization, e.g., $MgCO_3$). As part of this workflow, samples with low to intermediate carbonate reactivity volumes should be sent to the laboratory for more thorough analysis using the workflows defined below. If the proportion of the carbonate mineralization is less than 5%, the rock may be a suitable source rock for EHP exploration but will have limited potential for conventional or unconventional exploration for natural hydrogen. In some embodiments, upon determining that a geological source rock is potentially suitable for natural hydrogen exploration, the geological source rock may then be further investigated and used for natural hydrogen exploration.

Color Density Index

Because mafic minerals and their derivative alteration mineral phases tend to exhibit distinct colors and elevated densities with respect to typical sedimentary rocks, the color and density of samples (e.g., drill cuttings, hand samples, core) can also be indicative of a quality hydrogen source rock. Compared with rocks more commonly associated with oil and gas exploration, hydrogen source rocks commonly include minerals that appear vibrant or dark green (e.g., olivine, prehnite, pumpellyite, epidote, amphibole, glauconite, chlorite), red to reddish-brown (e.g., hematite), or intensely black (e.g., pyroxene, magnetite) when viewed under a light microscope (FIG. 9).

Color-calibrated light microscope digital images of mineral cuttings may be analyzed for their coloration using the RGB intensity of individual pixels to generate a percentage/intensity value after subtracting out the background. Machine learning models can be applied to images of known mineralogy to determine the composite Red, Green, and Blue values associated with olivine-, hematite-, and/or magnetite-rich rock and require a threshold intensity of Red and Green values across a minimum value of at least 20%, 30%, 40%, 50%, 60%, or 70% (e.g., 40%) of the image's pixels. This method would enable a process to rapidly analyze large image databases and filter samples to prioritize further analysis.

Many of the mineral phases associated with hydrogen generation are dense (e.g., hematite p=5.26 $g/cm^3$, magnetite p=5.18 $g/cm^3$, olivine=3.21 (forsterite)–4.27 (fayalite) $g/cm^3$, orthopyroxene=3.10 (enstatite)–4.02 (ferrosilite) $g/cm^3$) compared to minerals most commonly found in sedimentary rocks, for example (e.g., quartz p=2.65 $g/cm^3$, calcite ρ=2.71 $g/cm^3$, plagioclase ρ=2.62-2.76 $g/cm^3$). Density may be measured simply in the field by measuring the mass of the rock cuttings or core, then submerging the sample in water in a graduated vessel and measuring the associated displacement to determine volume, then density can be calculated according to the equation ρ=mass (g)/volume ($cm^3$). Sample density may also be measured with other analytical methods (e.g., pycnometry).

A simple alteration assessment that can be performed in the field (e.g., while drilling) determines the coloration index of an interval. If the green and/or red portions have minimum values exceeding, for example, 40% of the cuttings and the density of the sample can be measured and if it exceeds 2.72 $g/cm^3$ or is less than 2.5 $g/cm^3$, the interval can be flagged for containing potential hydrogen source rock material or prioritized for further geochemical analysis. Subsequent analyses (e.g., XRD, XRF) will be required to assess its suitability for past versus potential future generation of hydrogen.

Figure 13:
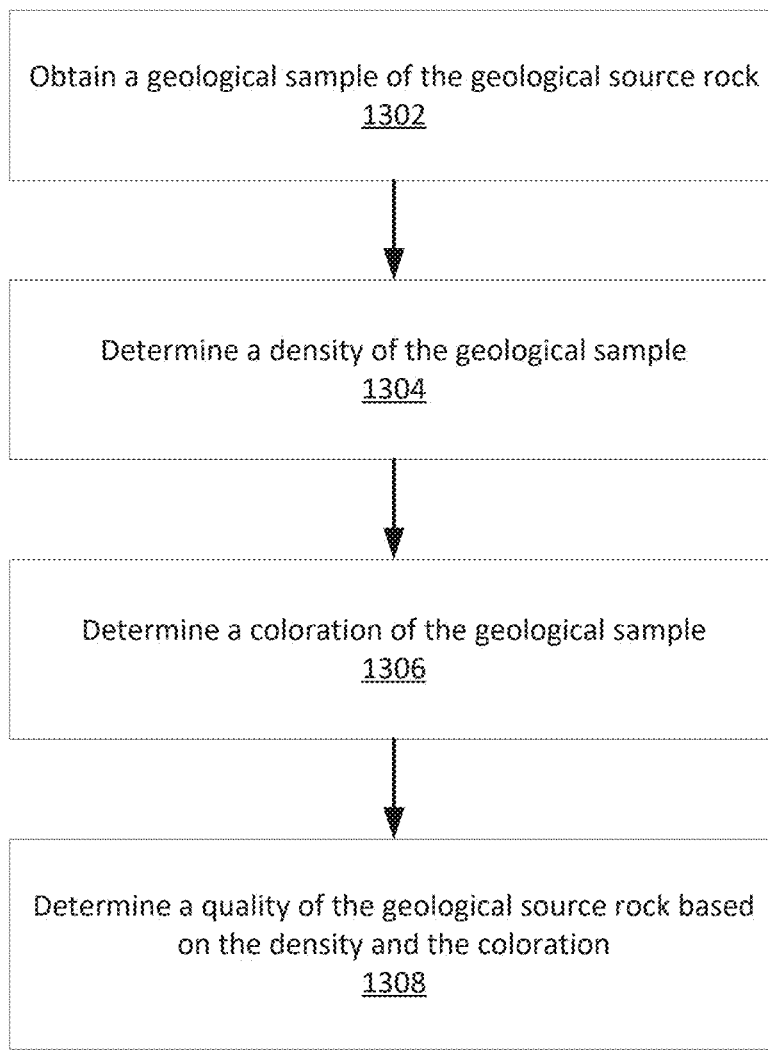
FIG. 13 shows example operations for evaluating hydrogen generation potential from a geological source rock based on the Color-Density Index, in accordance with some example embodiments described herein.

Turning to FIG. 13, example embodiments are shown for evaluating hydrogen generation potential from geological source rock, based on the density and coloration of samples of the geological source rock. In many cases, mineral colors are determined by the identity and oxidation states of the metal atoms incorporated in them. Additionally, the size and number of open valences of the metal ions may influence the density of the minerals which are formed. As such, the CDI represents a rapid and reliable means of evaluating geological samples of hydrogen source rocks.

As shown in operation 1302, the method includes using a drilling apparatus or sample repository to obtain a geological sample of a prospective hydrogen source rock. In some embodiments, the geological sample obtained could be obtained from a drilling site in the form of core samples, rock cuttings, or other standard sample varieties known in the art. In some embodiments, the geological sample obtained could be obtained from a repository of samples from known locations.

As shown in operation 1304, the method includes using analytical methods to determine a density of the geological sample. In some embodiments, samples may be used as-is for experimentation or may be processed in some way, such as by crushing, comminuting, and/or powdering. In some embodiments, mineral phases of the geological sample may be separated from one another before or after analysis. In some embodiments, sample density may be quantified through determining the mass of the sample, the volume of the sample, and finally calculating the density by dividing the mass of the sample by the volume of the sample. In some embodiments, the mass of the sample may be determined using a balance or other standard methods. In some embodiments, the volume of the sample may be determined by measuring a volume of water displaced by the sample or other standard methods. In some embodiments, the density may be determined by pycnometry or other methods known in the art.

As shown in operation 1306, the method includes using analytical methods to determine a coloration of the geological sample. In some embodiments, a visible light microscope with a detector capable of quantifying light may be used to analyze samples. In some embodiments, geological samples may be used as-is for experimentation or may be processed in some way, such as by crushing, cutting, comminuting, and/or powdering. In some embodiments, mineral phases of the geological sample may be separated from one another before or after analysis. In some embodiments, the detector capable of quantifying light may be a spectrophotometer, charge-coupled device, and/or similar device which may quantify light of different wavelengths separately and/or together. In some embodiments, the coloration of the geological samples may be quantified by recording a digital image of the geological sample and determining the amount of red, green, and blue light reflected from or transmitted through the geological samples at each pixel. In some embodiments, the coloration can be further quantified by determining an amount of pixels in the digital image which surpasses a minimum threshold of each red, green, and blue light.

As shown in operation 1308, data processing is performed to determine a quality of the geological source rock based on the density and the coloration. In some embodiments, the quality of the geological source rock may be the ability of the geological source rock to produce hydrogen or may simply be a classification of whether or not the geological sample merits additional analyses. In some embodiments, the color and the density of the geological sample may be used, in combination or alone, to assess the geological source rock's ability to generate hydrogen. In some embodiments, geological samples which have met certain coloration and density criteria may be determined to be of sufficient quality and the geological samples will be flagged for more analysis.

Using Magnetic Susceptibility to Determine a Mafic Alteration Index (MAI)

Magnetic susceptibility, a quantitative measurement of the extent to which a material may be magnetized in relation to a given applied magnetic field, can also be used in combination with normative or modal mineralogy to assess hydrogen source rock potential and maturity. $H_1$ and $H_2$ minerals display higher magnetic susceptibilities than most minerals unrelated to hydrogen generation (e.g., sedimentary rocks, quartz, plagioclase, alkali feldspars, non-iron bearing carbonates or clays). Importantly, the intensity of magnetic susceptibility varies accordingly to the $Fe^{3+}/Fe^{2+}$. As a result, the magnetic susceptibility will also vary according to the relative proportion of $H_1$ and $H_2$ mineral phases and can be used as a semi-quantitative proxy of the degree of hydrogen-generating mineral alteration that is indicative of past volumes of hydrogen generation.

As a result, the magnetic susceptibility of a rock sample can be used to assess the degree of maturity and iron content of bulk samples. An important advantage of this magnetic susceptibility embodiment is that magnetic susceptibility can be measured accurately and quickly in the field and allow for prioritization of other geochemical analyses. Thus, this method allows for rapid evaluation of any materials produced from drilling a well or borehole (e.g., drill cuttings, whole core, outcrop), field sampling, or following retrieval of samples from public or proprietary rock repositories.

Molar Estimates of Hydrogen Generation

The amount of hydrogen previously generated by alteration reactions that occurred, or the amount of hydrogen that could be generated when alteration reactions do occur, can be predicted if the mineralogy is well-constrained. Normative mineralogy calculations based on oxide data (measured from bulk elemental composition analyses such as XRF) can back-calculate proportions of $H_0$ and $H_1$ minerals as part of the original mineralogy of unaltered source rock.

Bulk elemental composition generated from rock samples in the laboratory or obtained from public or proprietary databases may be used to determine the normative mineralogy (i.e., an estimated idealized mineralogy based on typical minerals precipitated from an anhydrous magma using principals of geochemistry) of the rock using Cross-Iddings-Pirsson-Washington (CIPW), Barth-Niggli, or other normative calculations. Normative mineralogy calculations include assumptions about such geochemical concepts as initially anhydrous conditions, mineral incompatibility, etc. The output of these calculated norms consists of idealized initial mineral abundances (e.g., olivine %, orthopyroxene %, plagioclase %, etc.) formed after magma cooling and prior to hydrothermal alteration, which can be used as inputs into a hydrogen systems numerical model to serve as the "starting point" of an igneous rock before mineral alteration and hydrogen generation.

Most crucial to hydrogen generation are the olivine and pyroxene phases that the iron oxide content can be assigned to via CIPW calculations. The iron-rich portions of these minerals can generate hydrogen during alteration reactions (e.g., serpentinization) as described via stoichiometric equations (FIG. 1). A similar procedure can use the results from modal mineralogy to quantify the amounts of $H_{2a}$ and $H_{2b}$ minerals from the sample. Summation of the $H_1$ and $H_{2a}$ minerals enables an estimate of the moles of hydrogen that can be generated from further alteration of the rock (termed $M_1$) and likewise, summation of the moles of all $H_{2a}$ and $H_{2b}$ minerals enables an estimate of the moles of hydrogen that had been generated from past alteration of the rock (termed $M_2$).

The techniques above are combined to leverage increasingly specific data (FIG. 7) to evaluate hydrogen source rocks by defining $H_0$, $H_1$, and $H_2$ composition in accordance with the availability of increasingly complete datasets. The input data and outputs from these workflows are described in FIG. 8. The suitability of a rock as a source rock for past or future hydrogen generation needs to consider a combination of both the relative ratio of $H_1$ and $H_2$ minerals and the actual iron content in the rock. For example, a sample with dominantly $H_2$ minerals (e.g., antigorite and magnetite) with little residual $H_1$ mineral phases (e.g., forsterite and fayalite) would have a $H_2/H_1$ value approaching infinity (o), which would indicate that the hydrogen source rock has been extensively altered and that a volume of hydrogen corresponding to that ratio and the total molar abundance of iron was formed. Alternatively, a sample with dominantly $H_1$ mineral phases (e.g., forsterite and fayalite), but few $H_2$ minerals (e.g., antigorite and magnetite) would have a $H_2/H_1$ value approaching 0. In this case, even if the sample was rich in iron, the past generation of hydrogen would be anticipated to be minimal. Importantly, samples that display high ratios of $H_2/H_1$, but low total iron (or magnesium in the case of carbon mineralization) indicate the occurrence of extensive alteration, but low quantities of hydrogen generation.

To address this, the $H_2/H_1$ ratio needs to be scaled by the total iron content in the sample to evaluate the direct link between mineralogy and chemistry required for hydrogen generation and calculate a Hydrogen Source Relevance (HSR) following the calculation below:

$$HSR = \frac{H_2}{H_1} \times [Fe]_{total}$$

where the absence of iron in the oxide data would drop this HSR value to 0 and preclude the sample from representing a quality source rock. In some embodiments, an HSR score greater than 0.01, 0.02, 0.03, 0.04, 0.05, 0.06, 0.07, 0.08, 0.09, 0.10, 0.11, 0.12, 0.13, 0.14, or 0.15 and an iron content of greater than 1%, 2%, 3%, 4%, 5%, 6%, 7%, 8%, 9%, or 10% (e.g., [Fe]>7%) by weight indicates that the geological source rock is suitable for natural hydrogen production generation.

By establishing balanced stoichiometric equations that represent the alteration reactions of each mineral that can release or has released hydrogen, the moles of hydrogen generated on a per mass of rock basis can be estimated and used to assess hydrogen source rock quality of the sample. Below, these equations are presented with increasingly specific data inputs, starting with mineralogy data only (e.g., normative mineralogy, modal mineralogy), then adding in iron concentration of individual mineral phases (XRD, SEM/EDS), then adding in the iron valence ratio of secondary phases (Mössbauer spectrometry), and finally adding in relative reaction kinetics for each mineral, using computer simulations, literature values, or laboratory analysis.

Starting with the $M_1$ reactions, the simplest estimate of hydrogen generation uses the mineralogy of a sample to sum contributions from multiple stoichiometric equations that account for the moles of hydrogen generated from each mole of a given mineral:

$$M_1 = m_{rock} \cdot \sum_i^P \frac{\mu_i}{MW_i} \cdot \sigma_i$$

where $m_{rock}$ is the mass of sample being analyzed, $MW_i$ is the molecular weight of mineral i in kg/mol, and $\sigma_i$ is the stoichiometric ratio of moles of hydrogen generated from moles of mineral i. This equation is summed across all P minerals involved in the $M_1$ reactions, which for hydrogen source rock potential will include all $H_1$ and $H_2a$ minerals, to get the total moles that can potentially be generated for a given mass of rock if the rock is stimulated through natural or engineered processes.

This model can be improved through laboratory analysis (XRD, SEM/EDS) by accounting for the iron-rich phases of minerals (e.g., accurate proportions of fayalite vs. forsterite in olivine) to constrain the stoichiometry using iron concentration of each mineral i ($X_i$):

$$M_1 = m_{rock} \cdot \sum_i^P X_i \frac{\mu_i}{MW_i} \cdot \sigma_i$$

Furthermore, for phases which can contain both $Fe^{2+}$ and $Fe^{3+}$ iron in their mineral structure, Mössbauer mass spectrometry of secondary minerals (particularly clays and low temperature and pressure metamorphic facies) can measure the ratio of $Fe^{2+}/Fe_{total}$ of iron in mineral i ($Y_i$) which further constrains the molar output:

$$M_1 = m_{rock} \cdot \sum_i^P X_i \cdot Y_i \frac{\mu_i}{MW_i} \cdot \sigma_i$$

Finally, the kinetics of hydrogen generation reactions may preclude alteration of a mineral based on the rate of reaction for some minerals compared to others, rendering their reactions less relevant to engineered stimulation (e.g., EHP) that occurs on the minutes to weeks timescale. The kinetic rates of these reactions will strongly depend on geochemical and geophysical conditions (e.g., pressure, temperature, Eh, pH, salinity) of the system as well as the mineral itself (e.g., phase, average grain size, chemical composition). Through kinetic experiments, literature values, and/or computer simulations, kinetic factors ($k_i$) that describe how rapidly the alteration reaction proceeds (e.g., the speed at which the alteration reaction proceeds) can be determined for each mineral. The kinetic rate variable, $k_i$, is a unitless quantity. Incorporating $k_i$ into the equation for $M_1$ allows for a comprehensive stoichiometric estimate of hydrogen generation:

$$M_1 = m_{rock} \cdot \sum_i^P k_i \cdot X_i \cdot Y_i \frac{\mu_i}{MW_i} \cdot \sigma_i$$

Similarly, the moles of hydrogen generated by completed reactions ($M_2$) can be calculated as:

$$M_2 = m_{rock} \cdot \sum_i^C X_i \cdot Z_i \frac{\mu_i}{MW_i} \cdot \sigma_i$$

where $m_{rock}$ is the mass of sample being analyzed, $X_i$ is the iron concentration of mineral i, $Z_i$ is the ratio of $Fe^{3+}/Fe_{total}$ of iron in mineral i, $MW_i$ is the molecular weight of mineral i in kg/mol, and $\sigma_i$ is the stoichiometric ratio of moles of hydrogen generated from moles of mineral i. This equation is summed across all C minerals involved in the $M_2$ reactions, which for hydrogen source rock potential will include all $H_{2a}$ and $H_{2b}$ minerals, to get the total moles generated for a given mass of rock from past alteration reactions. Note that kinetics are not considered in the $M_2$ calculation because the reactions have already completed. In some embodiments, the hydrogen source rock components may be evaluated based on the estimated quantity of moles of hydrogen generated per unit rock.

In some embodiments, the systems disclosed herein may include a computing device having at least one processor and a memory storage storing data and one or more operational programs thereon for implementing certain steps of the methods disclosed herein. The memory storage (e.g., a non-transitory memory storage medium) is in electronic communication with the processor in electronic communication. The system includes a communication network in electronic communication with the computing device.

The computing device may include one or more servers, one or more computers (e.g., desktop, laptop, etc.), or one or more mobile computing devices (e.g., smartphone, tablet, etc.). The processor of the computing device includes hardware for executing instructions (e.g., instructions for carrying out one or more portions of any of the methods disclosed herein), such as those making up an operational program.

The processor is configured to read and execute operational programs stored in the memory storage.

The memory storage of the computing device may include one or more of volatile and non-volatile memories, such as Random Access Memory (RAM), Read Only Memory (ROM), a solid state disk (SSD), Flash, Phase Change Memory (PCM), or other types of data storage. The memory storage may be internal or distributed memory. The one or more operational programs stored in the memory storage may include machine readable and executable instructions for performing any of the portions of the methods disclosed herein. For example, the operational programs may include instructions for determining one or more properties of iron in the geological sample and performing a hydrogen quantification operation based on the one or more properties of iron to determine a potential for hydrogen production without injection of a reactant. In other embodiments, the operational programs may include instructions for performing the hydrogen quantification operation comprises quantifying a volume of hydrogen based on any of the equations disclosed herein. In still further examples, the operational programs may include instructions for determining oxide data and carbonate reactivity of the geological sample as disclosed herein. In still further examples, the operational programs may include instructions for determining a density and a coloration of the geological sample to determine a coloration index thereof, as disclosed herein. The memory storage also has a data storage therein for storing one or more sets of data, outputs of the methods disclosed herein, or any other digital information used in the methods disclosed herein.

Geological Hydrogen Source Rock Scoring

The relative proportions of minerals in a rock that are related to hydrogen generation (either past or future) can be used to quantify the rock's suitability to serve as a source of hydrogen. Two specific metrics are defined for Source Rock Maturity (SRM) and Source Rock Potential (SRP):

$$SRM = \frac{H_{2a} + H_{2b}}{H_0 + H_1 + H_2} \times 100\% \text{ and } SRP = \frac{H_1 + H_{2a}}{H_0 + H_1 + H_2} \times 100\%.$$

By way of example, using three endmembers, SRM and SRP can be conceptualized as follows: 1) For a rock composed exclusively of altered $H_{2b}$ minerals that will not undergo future alteration and produce more hydrogen (e.g., a serpentinite comprised of 100% lizardite and magnetite), the SRM=100% (i.e., all iron has been oxidized and the rock cannot produce more hydrogen) and the SRP=0%, as the rock has generated its maximum amount of hydrogen and cannot produce any more; 2) For a rock composed exclusively of unaltered $H_1$ minerals (e.g., peridotite comprised of iron-rich olivine), SRM=0 (i.e., no iron has been oxidized and thus no hydrogen has formed) and SRP=100%, as the entire rock has the potential to produce hydrogen; and 3) For a rock composed exclusively of $H_0$ associated minerals (e.g., sedimentary rock comprised of 100% quartz, carbonates, and feldspars), both SRM and SRP equal 0%, as the rock has no relevance to past or future hydrogen generation. The majority of potential source rocks will have SRM and SRP scores both between 0% and 100% and provide a sliding scale of suitability for hydrogen generation, either as source rocks indicating possible accumulation in overlying formations or as targets to be artificially stimulated (e.g., through EHP).

In one example embodiment, a geological rock sample includes the following values:

| Mineral | Mineral Category | Volume of Sample % |
|---|---|---|
| Hematite | $H_{2b}$ | 20% |
| Magnetite | $H_{2a}$ | 10% |
| Chlorite | $H_{2a}$ | 10% |
| Olivine | $H_1$ | 5% |
| Biotite | $H_0$ | 5% |
| Plagioclase | $H_0$ | 20% |
| Calcite | $H_0$ | 10% |
| Gypsum | $H_0$ | 10% |

This geological rock sample yields an SRM score of 44.4% and an SRP score of 27.8%.

In some embodiments, a geological sample yielding an SRM score greater than 20% indicates that the geological source rock is a suitable rock source for natural hydrogen exploration. In some embodiments, an SRM score greater than 1%, 2%, 3%, 4%, 5%, 6%, 7%, 8%, 9%, 10%, 11%, 12%, 13%, 14%, 15%, 20%, 25%, 30%, 35%, 40%, or 50% indicates that the geological source rock is a suitable rock source for natural hydrogen exploration.

In some embodiments, a geological sample yielding an SRP score greater than 0.5% indicates that the geological source rock is a suitable rock source for natural hydrogen exploration. In some embodiments, an SRP score greater than 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10.0% indicates that the geological source rock is a suitable rock source for natural hydrogen exploration.

In practice, not only are the SRM and SRP ratios important to score hydrogen source rock, but magnitudes of the $M_1$ and $M_2$ estimates must also be considered (i.e., two rocks with SRP of 75% will be scored differently if the first can generate only 1 mol of hydrogen per unit mass of rock while the second can generate 1,000 moles of hydrogen per unit mass of rock).

Evaluating Source Rocks in Natural Hydrogen Systems

Using the methods disclosed herein for evaluating natural hydrogen source rocks, lithologic samples can be scored based on both quality (e.g., source rock maturity and source rock potential) and estimates of the volume of hydrogen generation based on its mineralogy. From this output, the hydrogen exploration approaches described above (e.g., source rock mapping, reservoir mapping, basin analyses, hydrogen systems models) can be used to develop hydrogen systems models that include migration, reservoir, trap, seal, and preservation.

When exploring for "conventional" natural hydrogen targets, the ideal natural hydrogen source rock will have a high initial proportion of $H_1$ and $H_2$ minerals (i.e., minerals rich in iron and other mafic components) and a low proportion of $H_0$ minerals. Mature hydrogen source rocks will also be dominated by elevated levels of hydrogen-generating mineral phases that have already generated significant amounts of hydrogen. The highest quality source rocks for "conventional" natural hydrogen exploration will exhibit a high score for hydrogen source relevance, which incorporates both elevated iron content and high $H_2/H_1$, an elevated mafic alteration index/magnetic susceptibility, an elevated source rock maturity index, a high HAI score, and a high proportion of dense minerals with high proportions of red and green colors. One embodiment develops a method for scoring and ranking high-quality source rocks using the methods disclosed above for "conventional" hydrogen exploration based on measuring and identifying rocks with a high initial proportion of $H_1$ and $H_2$ minerals on a volumetric basis that have a present mineralogy dominated by $H_2$ mineral phases. Additional and standard exploration workflows are required to identify specific targets for "conventional" natural hydrogen exploration in these geologic settings based on mapping migration pathways, prospective reservoirs, prospective trapping geometries, and prospective scaling lithologies. Importantly, this embodiment can be used to score and rank prospective hydrogen systems at various scales. For illustrative purposes, this can include on global scales, within a particular region, within a country, within a basin or system, or even within a borehole.

In "unconventional" natural hydrogen exploration, high-quality source rocks will display a high initial proportion of $H_1$ and $H_2$ minerals on a volumetric basis that have a present mineralogy dominated by $H_2$ mineral phases. The highest quality source rocks for "unconventional" natural hydrogen exploration will exhibit a high score for hydrogen source relevance, which incorporates both elevated iron content and high $H_2/H_1$, an elevated mafic alteration index/magnetic susceptibility, an elevated source rock maturity index, a high HAI score, and a high proportion of dense minerals with high proportions of red and green colors. One embodiment develops a method for scoring and ranking high-quality source rocks for "unconventional" natural hydrogen exploration using the methods disclosed above based on measuring and identifying rocks with a high initial proportion of $H_1$ and $H_2$ minerals on a volumetric basis that have a present mineralogy dominated by $H_2$ mineral phases. Additional and standard exploration workflows are required to identify specific targets for "unconventional" natural hydrogen exploration in these settings. Importantly, this embodiment can be used to rank prospective hydrogen systems at various scales. For illustrative purposes, this can include on global scales, within a particular region, within a country, within a basin or system, or even within a borehole.

Low Carbon Intensity Hydrogen

There is a significant focus today on the decarbonization of energy and chemical industries to positively impact climate change. In response, companies and individuals are actively working to produce cost-effective "clean" or "green" hydrogen and other chemicals. Hydrogen is labelled as "green" when its production results in significantly lower greenhouse gas emissions compared to the production of other energy sources. Governments have recently begun to categorize hydrogen by assessing the emissions intensity of the production plant or system from which the hydrogen is sourced. Specifically, components or portions of the hydrogen gas production process, including the hydrogen feedstock from a wellhead as well as the hydrogen gas product, can be assigned a carbon intensity (CI) score according to the greenhouse gas emissions resulting from the particular component or portion. The CI scores referenced herein are provided in kg $CO_2$ equivalent greenhouse gases per kg hydrogen produced (kg $CO_{2eq}$/kg $H_2$).

In some embodiments, the geologic source rock identified by the methods and systems described herein as suitable sources for hydrogen exploration and/or hydrogen accumulation provide a feedstock including hydrogen gas. Feedstock extracted from boreholes into the subsurface from wellheads may be of a sufficient composition that it can be subsequently separated and/or purified to between about 90% and about 99.9999% purity, meeting the needs of the hydrogen markets.

In some examples, the feedstock includes primarily hydrogen gas. The feedstock may also include additional gas constituents such as nitrogen, carbon dioxide, methane and noble gases such as helium, neon, argon, xenon, krypton, or radon. In some examples, the feedstock has a CI score of less than 4.0 kg $CO_2$eq/kg $H_2$, or less than 3.0 kg $CO_2$eq/kg $H_2$, or less than 1.5 kg $CO_2$eq/kg $H_2$, or less than 0.45 kg $CO_2$eq/kg $H_2$. For example, a feedstock that includes at least 50 mol %, 60 mol %, 70 mol %, 75 mol %, 80 mol %, 85 mol %, 90 mol %, 95 mol %, 98 mol %, or 99 mol % hydrogen, less than 15 mol %, 12.5 mol %, 10 mol %, 9 mol %, 8 mol %, 7 mol %, 6 mol %, 5 mol %, 4 mol %, 3 mol %, 2 mol %, 1 mol %, 0.5 mol %, or 0.1 mol % carbon dioxide, less than 12.5 mol %, 10 mol %, 9 mol %, 8 mol %, 7 mol %, 6 mol %, 5 mol %, 4 mol %, 3 mol %, 2 mol %, 1 mol %, 0.5 mol %, or 0.1 mol % methane ($CH_4$), and up to 50 mol %, 45 mol %, 40 mol %, 35 mol %, 30 mol %, 25 mol %, 20 mol %, 15 mol %, 12.5 mol %, 10 mol %, 9 mol %, 8 mol %, 7 mol %, 6 mol %, 5 mol %, 4 mol %, 3 mol %, 2 mol %, or 1 mol % nitrogen provides a CI score of less than 4.0, 3.0, 1.5, or 0.45 kg $CO_2$eq/kg $H_2$. In such cases, the hydrogen produced or obtained from these geological sources may be classified as low carbon intensity hydrogen.

Global Evaluations of Available Geochemical and Mineralogical Data

One challenge when evaluating hydrogen source rocks is the availability of data to evaluate hydrogen source rock viability, along with the excessive costs of drilling wells and collecting samples to evaluate these components. Key data needs for the evaluation process include bulk elemental composition, determination of the key mineral assemblages, the iron content of each iron-bearing mineral phase, and the oxidation state of that iron in each mineral (i.e., $Fe^{3+}/Fe_{total}$ or $Fe^{2+}/Fe_{total}$).

In some cases, these data may already exist in public, academic, or proprietary databases. For example, oxide data (e.g., from XRF measurements) are commonly provided in tabular form, allowing the series of equations described in the calculation of the CIPW-NORM to be run simultaneously for multiple samples. As such, algorithms have been developed to run the equations automatically (e.g., using Excel spreadsheets or scripting languages such as Python) as new oxide data become available and the outputs from these routines provide mineralogical information (and thereby moles of hydrogen generated) that can be associated with the sample inputs. The CIPW-NORM mineralogy outputs for each sample can then be classified into the various $H_0$, $H_1$, and $H_2$ mineral categories and quantitatively compare samples automatically. These oxide values can come from a single borehole to provide a mineralogical description with respect to depth or from a field study in an area of interest, but sample locations are not geographically restricted.

Public or proprietary rock, drill cuttings, or core databases may contain major elemental composition, and less frequently, complete mineral assemblage data. Physical rock samples may also be collected from public or proprietary repositories, outcrops at the surface, cuttings/core from drilled boreholes, among other resources, and analyzed in the laboratory for chemical and mineralogical parameters needed for source rock evaluation, including bulk elemental composition, mineral assemblage, mineral iron content, and iron oxidation state.

CONCLUSION

It is noted that there is no requirement to provide or address the theory underlying the novel and groundbreaking systems, methods, performance or other beneficial features and properties that are the subject of, or associated with, embodiments of the present disclosure. Nevertheless, various theories are provided in this specification to further advance the art in this critical area, and in particular in the important area of hydrogen, dihydrogen sulfide, carbon dioxide, and helium exploration, production, and downstream conversion or utilization. These theories put forth in this specification, and unless expressly stated otherwise, in no way limit, restrict or narrow the scope of protection to be afforded the claimed embodiments. It is further understood that the present disclosure may lead to new, and heretofore unknown theories to explain the conductivities, hydrogen generation rates, drainages, resource production, chemistries, and function-features of embodiments of the methods, articles, materials, devices, and system of the present disclosure and that such later developed theories shall not limit the scope of protection afforded the present disclosure. Other embodiments than those specifically disclosed herein may be included without departing from its spirit or essential characteristics. The embodiments disclosed are to be considered in all respects only as illustrative and not restrictive. The various aspects and embodiments disclosed herein are for purposes of illustration and are not intended to be limiting. The various embodiments of devices, systems, activities, methods, and operations set forth in this specification may be used with, in, or by, various processes, industries, and operations, in addition to those embodiments of the Figures and disclosed in this specification. The various embodiments of devices, systems, methods, activities, and operations set forth in this specification may be used with other processes, industries, and operations that may be developed in the future; with existing processes, industries, and operations, which may be modified, in-part, based on the teachings of this specification; and with other types of gas recovery and valorization systems and methods.

Further, the various embodiments of devices, systems, activities, methods, and operations set forth in this specification may be used with each other in different and various combinations. Thus, the configurations provided in the various embodiments of this specification may be used with each other. For example, the components of an embodiment having A, A', and B and the components of an embodiment having A", C, and D can be used with each other in various combinations (e.g., A, C, D, and A; A", C, and D; etc.) in accordance with the teaching of this specification. Thus, the scope of protection afforded by the present inventions should not be limited to a particular embodiment, configuration or arrangement that is set forth in a particular embodiment, example, or in an embodiment in a particular Figure. Terms of degree (e.g., "about," "substantially," "generally," etc.) indicate structurally or functionally insignificant variations. In an example, when the term of degree is included with a term indicating quantity, the term of degree is interpreted to mean ±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

What is claimed is:

1. A method for evaluating hydrogen generation potential from a geological source rock, the method comprising:
obtaining a geological sample of the geological source rock;
determining one or more properties of iron in the geological sample by measuring, via Mössbauer spectroscopy, an abundance of $Fe^{3+}$ and an abundance of $Fe^{2+}$ in the geological sample; and
performing a hydrogen quantification operation based on the one or more properties of iron to determine a potential for hydrogen production without injection of a reactant, the hydrogen quantification operation comprising measuring a proportion of $Fe^{2+}$ to $Fe^{3+}$ wherein a potential volume of hydrogen that may be generated is quantified based on the proportion of $Fe^{2+}$ to $Fe^{3+}$.

2. The method of claim 1, wherein the one or more properties of iron in the geological sample is a concentration or a species of iron.

3. The method of claim 1, wherein determining the one or more properties of iron comprises measuring minerals of the geological sample through one of:
   i. using x-ray diffraction, scanning electron microscope-energy dispersive X-ray spectroscopy, or optical mineralogy,
   ii. measuring an abundance of minerals with $Fe^{2+}$, directly measuring an iron content using x-ray fluorescence, neutron activation, Inductively Coupled Plasma Mass Spectrometry (ICP-MS), and Inductively Coupled Plasma Optical Emission Spectrometry (ICP-OES) of the geological sample, and apportioning the iron content between the minerals with $Fe^{2+}$;
   iii. measuring an abundance of minerals with $Fe^{2+}$, separating the minerals with $Fe^{2+}$, and directly measuring an iron content of individual phases of minerals without $Fe^{2+}$; or
   iv. measuring an iron content using x-ray fluorescence, neutron activation, ICP-MS, or ICP-OES.

4. The method of claim 1, wherein the one or more properties of iron in the geological sample is a species of iron, and wherein the species of iron comprises one of a mineral or an oxidation state.

5. The method of claim 1, wherein performing the hydrogen quantification operation further comprises quantifying a volume of hydrogen generated over geologic time.

6. The method of claim 5, wherein the step of quantifying the potential volume of hydrogen that may be generated comprises calculating a value $M_1$ for each mineral of the geological sample:

$$M_1 = m_{rock} \cdot \sum_i^P \frac{\mu_i}{MW_i} \cdot \sigma_i$$

where $m_{rock}$ is a mass of sample being analyzed, $\mu_i$ is a relative abundance of mineral i in the sample, $MW_i$ is a molecular weight of mineral i in kg/mol, and $\sigma_i$ is a stoichiometric ratio of moles of hydrogen generated from moles of mineral i.

7. A method for evaluating hydrogen generation potential from a geological source rock, the method comprising:
obtaining a geological sample of the geological source rock;
determining one or more properties of iron in the geological sample by measuring, via Mössbauer spectroscopy, an abundance of $Fe^{3+}$ and an abundance of $Fe^{2+}$ in the geological sample; and
performing a hydrogen quantification operation based on the one or more properties of iron to determine a potential for hydrogen production without injection of a reactant, the hydrogen quantification operation comprising measuring a proportion of $Fe^{2+}$ to $Fe^{3+}$ wherein a potential for carbon mineralization or a sulfur mineralization is quantified based on the proportion of $Fe^{2+}$ to $Fe^{3+}$.

8. An analytical instrumentation system for evaluating hydrogen generation potential from a geological source rock, the analytical instrumentation system comprising:

sample containers configured to contain a geological sample of the geological source rock; and analytical instrumentation configured to determine one or more properties of iron in the geological sample, wherein the analytical instrumentation comprises:

a Mössbauer spectrometer configured to measure an abundance of $Fe^{3+}$ and an abundance of $Fe^{2+}$ in the geological sample; and a computing device having a processor and memory storage operably coupled to the processor, the memory storage storing machine readable and executable instructions that, when executed, cause the computing device to:

determine one or more properties of iron in the geological sample; and perform a hydrogen quantification operation based on the one or more properties of iron to determine a potential for hydrogen production without injection of a reactant, the hydrogen quantification operation comprising measuring a proportion of $Fe^{2+}$ to $Fe^{3+}$, wherein a potential volume of hydrogen that may be generated is quantified based on the proportion of $Fe^{2+}$ to $Fe^{3+}$.

9. The analytical instrumentation system of claim 8, wherein the one or more properties of iron in the geological sample is a concentration or a species of iron.

10. The analytical instrumentation system of claim 8, wherein the one or more properties of iron in the geological sample is a species of iron, and wherein the species of iron comprises one of a mineral or an oxidation state.

11. The analytical instrumentation system of claim 8, wherein performing the hydrogen quantification operation further comprises quantifying a volume of hydrogen generated over geologic time.

* * * * *